United States Patent
Baggaley et al.

[11] Patent Number: 5,869,299
[45] Date of Patent: Feb. 9, 1999

[54] PROCESS FOR PRODUCING CLAVULANIC ACID

[75] Inventors: Keith Howard Baggaley, Redhill; Neville Hubert Nicholson, Dorking, both of England; Stephen William Elson, Madrid, Spain; Jeffrey Edwards, Worthing; Alison Jane Earl, Steyning, both of England; William Henry Holms, Glasgow; David Michael Mousdale, Netherton, both of Scotland; Jack Edward Baldwin, Hinksey Hill; Christopher Schofield, Cumnor Hill, both of England

[73] Assignee: SmithKline Beecham p.l.c., United Kingdom

[21] Appl. No.: 446,806

[22] PCT Filed: Nov. 26, 1993

[86] PCT No.: PCT/GB93/02442

§ 371 Date: Aug. 25, 1995

§ 102(e) Date: Aug. 25, 1995

[87] PCT Pub. No.: WO94/12654

PCT Pub. Date: Jun. 9, 1994

[30] Foreign Application Priority Data

Dec. 2, 1992 [GB] United Kingdom .................. 9225151
Dec. 2, 1992 [GB] United Kingdom .................. 9225152
Mar. 9, 1993 [GB] United Kingdom .................. 9304761

[51] Int. Cl.$^6$ .......................... C12N 9/80; C07D 205/08
[52] U.S. Cl. .................. 435/106; 536/23.2; 536/23.7; 540/362; 564/226; 564/230; 435/228
[58] Field of Search .................................. 435/228, 106; 536/23.2, 23.7; 540/362; 564/226, 230

[56] References Cited

U.S. PATENT DOCUMENTS 5,118,617  6/1992  Ortega et al. .......................... 435/69.1

FOREIGN PATENT DOCUMENTS 0 213 914  3/1987  European Pat. Off. ...... C07D 498/04
0 349 121  3/1990  European Pat. Off. ........ C12N 15/00

OTHER PUBLICATIONS

Brown, et al., Structures of Three Novel β–Lactams isolated from *Streptomyces clavuligerus*, *J.C.S. Chem. Comm*, pp. 282–283 (1979).

Baggaley, et al., "Studies on the Biosynthesis of Clavulanic Acid, Part 4.$^1$ Synthetic Routes to the Monocyclic β–Lactam Precursor, Proclavaminic Acid", *J. Chem Soc. Perkin Trans. 1*, pp. 1513–1520 (1990).

Baggaley, et al., "Studies on the Biosynthesis of Clavulanic Acid. Part 5.$^1$ Absolute Stereochemistry of Proclavaminic Acid, the Monocyclic Biosynthetic Precursor of Clavulanic Acid", *J. Chem Soc. Perkin Trans. 1*, pp. 1521–1533 (1990).

Chemical Abstracts, vol. 113, No. 3, 16 Jul. 1990, Abstract No. 18542q.

Chemical Abstracts, vol. 105, No. 21, 24 Nov. 1986, Abstract No. 187381b.

*Primary Examiner*—James Ketter
*Attorney, Agent, or Firm*—Zoltan Kerekes; William T. King; Edward T. Lentz

[57] ABSTRACT

A process for preparing clavulanic acid and other clavam derivatives using an enzyme system from Streptomyces, particularly *S. Clavuligerus*.

26 Claims, 3 Drawing Sheets

PROCESS FOR PRODUCING CLAVULANIC ACID

The present invention relates to the preparation of novel compounds by enzymic reactions, specifically the preparation of b- lactams particularly clavams such as clavulanic acid by the action of enzymes on appropriate precursors.

Clavulanic acid is Z-(2R,5R)-3-(b-hydroxy-ethylidene)-7-oxo-4-oxa-1-azabicyclo[3.2.0] heptane-2-carboxylic acid.

Clavulanic acid is a potent inhibitor of b-lactamase enzymes and is a compound of great clinical value since it protects b-lactamase-labile b-lactam antibiotics from degradation.

British Patent Specification No. 1 508 977 describes a clavam derivative known as clavulanic acid, which is a compound produced by *Streptomyces clavulilerus* ATCC 27064 or a high yielding mutant thereof.

The biosynthetic route to the important product clavulanic acid a key ingredient of the antibiotic AUGMENTIN (Trade Mark ) has been the subject of considerable study. It has been reported in EP A 0 213 914 that clavulanic acid is formed by the action of a series of enzymes on a precursor proclavaminic acid (F)

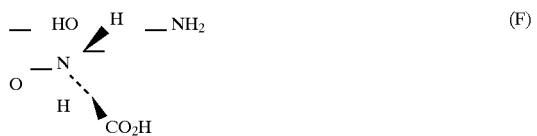
(F)

The earlier steps in the biosynthetic pathway have been more difficult to elucidate however the precise sequence of events has not hitherto been elucidated. Tests for assessing the utilisation of arginine and ornithine as specific precursors for clavulanic acid are described in *Appl. Environ Microbiol.* 1986, 52(4), 892–7.

We have now identified new intermediates and processes for their conversion into clavulanic acid. Accordingly the present invention provides a process for preparing clavulanic acid and other clavam derivatives from any one of compounds of formula (I)

(I)

wherein $R^1$ is

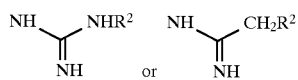

wherein $R^2$=H or $C_{1-6}$ alkyl or compounds of formula (II)

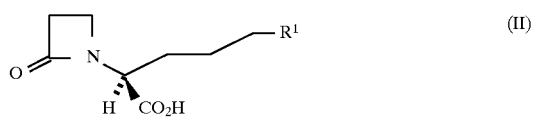
(II)

wherein $R^1$ is

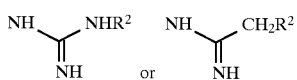

where $R^2$=H or $C_{1-6}$ alkyl or compounds of formula (III)

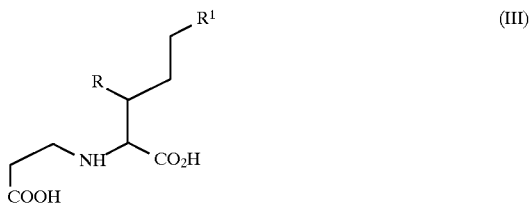
(III)

wherein R is H or OH
and wherein $R^1$ is

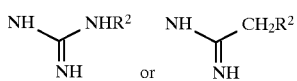

where $R^2$=H or $C_{1-6}$ allyl,
using an enzyme system from Streptomyces, preferably *S. clavuligerus*.

By 'other clavams' we mean compounds containing a 7-oxo-4-oxa-1-azabicyclo[3.2.0]heptane nucleus [J.C.S., Chem. Commun. (1979), 282].

Accordingly the present invention provides new compounds useful in the preparation of clavams in particular clavulanic acid. According to the present invention there is provided a compound of formula (I):

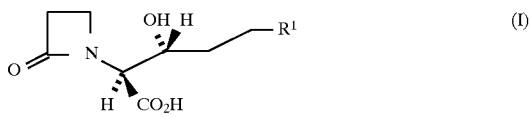
(I)

wherein $R^1$ is

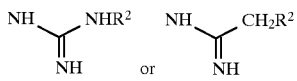

wherein $R^2$=H or $C_{1-6}$ alkyl.

We have now found that a precursor of compound (F) is a compound of formula (C):

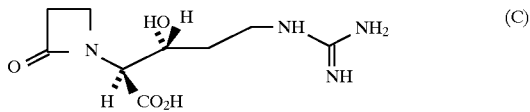
(C)

Accordingly in a preferred aspect there is provided a compound (C):which is threo-3-hydroxy-5-guanidino-2-(2-oxo-azetidin-1-yl) pentanoic acid preferably (2S-3R) or derivatives thereof.

Compound [C] can be prepared by reacting

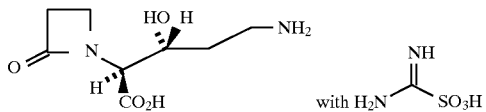

according to the method of J. E. Miller and J. J. Bischoff, Synthesis 1986, 777, or related methods known in the art.

According to the present invention there is also provided an enzyme having amidinohydrolase activity which is capable of removing the elements of urea from compounds bearing a guanidino group and in particular for converting (C) into (F) under suitable conditions.

Suitably the enzyme system is derived from a microorganism, in particular a species of Streptomyces. Preferably the enzyme is prepared from Streptomyces according to Example 1 described hereinafter. Alternatively, the enzyme may be produced from a recombinant source.

The enzyme may additionally be useful in converting a guanidino group into an amino group when caused to react with other substrates, for example (2S)-5-guanidino-2-(2-oxo-azetidin-1-yl)pentanoic acid (Compound B as defined below).

The enzyme having amidinohydrolase activity (hereinafter amidino hydrolyase) is obtainable from Streptomyces species, preferably *Streptomyces clavuligerus*. The amidinohydrolase enzyme is preferably in purified form, advantageously substantially pure form.

In a further aspect of the invention there is provided a method of preparing the amidinohydrolase by treating *S. clavuligerus* mycelium by centrifugation and ultrasonification followed by fractionation by ion-exchange chromatography.

In yet a further aspect of the invention there is provided a protein having amidinohydrolase activity having substantially the sequence of amino acids in SEQUENCE ID no. 1 hereinbelow.

The sequence in SEQUENCE ID no. 1 was obtained from the gene sequence of the DNA encoding the amidinohydrolase. The gene was identified by sequencing the N-terminus of the amidinohydrolase enzyme obtained from *S clavuligerus* and matching the sequence to that predicted from an open reading frame found in a portion of *S clavuligerus* chromosomal DNA which had been cloned on a vector known as pBROC 44. The preparation of pBROC 44 is described in Example 6 of EP-A-0349 121.

In a further aspect the present invention also provides DNA consisting essentially of a gene encoding the amidinohydrolase. The present invention also provides a vector (other than pBROC 44) comprising such DNA, preferably an expression vector for expression of amidinohydrolase in a suitable host organism.

It will be understood that the DNA is not in its 'natural' state (as it occurs in nature) but is in isolated or substantially purified form. Preferably the DNA of the present invention is derived from *S. clavuligerus*, however the invention also encompasses DNA sequences derived from other suitable organisms especially clavulanic producing organisms other than *S. clavuligerus* which hybridise, preferably under conditions of high stringency, with the DNA in SEQ. ID No.2 or a subfragment thereof and which code for an enzyme with amidinohydrolase activity.

The DNA of the invention and vectors containing same may find use in many areas of industrial activity. That also applies to host microorganisms transformed with said vectors and the enzymes they express. For example recombinant vectors containing said DNA may be of value, when transformed into suitable hosts, in the production of genetically modified microorganisms which synthesize increased amounts of clavulanic acid Preferably the DNA has substantially the sequence shown in SEQUENCE ID no. 2 hereinbelow or has a sequence which is degenerate to this sequence but encodes the amino acid sequence of SEQUENCE ID no. 1. The invention also extends to any mutant or related sequence which encodes an enzyme having amidinohydrolase activity.

According to the invention there is provided a process for preparing proclavaminic acid by contacting a compound of formula [C] or a salt or protected form thereof or analogues thereof with an enzyme having amidino-hydrolase activity.

The present invention also provides a compound of formula (II):

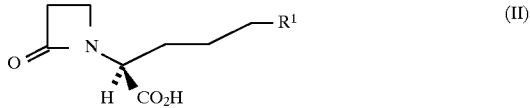

wherein $R^1$ is

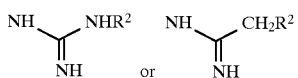

where $R^2 = H$ or $C_{1-6}$ alkyl.

In a preferred aspect there is provided a compound (B):

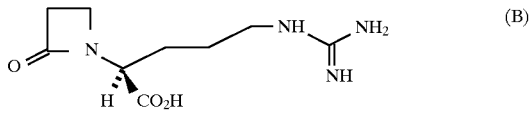

which is (2S)-5-guanidino-2-(2-oxo-azetidin-1-yl) pentanoic acid (B), or derivatives thereof.

Compound [B] can be prepared by reacting

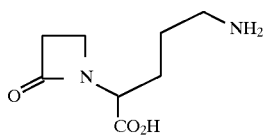

with

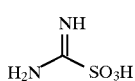

according to the method of J. E. Miller and J. J. Bischoff, Synthesis 1986, 777, or related methods known in the art.

According to the invention there is provided also a process for preparing C by contacting a compound of formula [B] or a salt or protected form thereof or analogues thereof with an enzyme having hydroxylation activity, in particular one having clavaminic acid synthase activity. Preferably the enzyme system is derived from a microorganism, in particular a species of Streptomyces. Alternatively, the enzyme may be produced from a recombinant source. Preferably the enzyme is clavaminic acid synthase (CAS) as described in EP-A-213 914. The present invention relates to both CAS prepared from a normal clavulanic acid producing strain of *Streptomyces clavuligerusas* well as 'recombinant' CAS which can be obtained according to the methods in EP 349121 or for example, from an *E. coli* into which the CAS gene had been cloned in an expression vector, particularly the vector pBROC 413 [a non transferable derivative of pT 7.7(Tabor, S., & Richardson, C. C. (1985) Proc. Natl. Acad. Sci.USA, 82, 1074–1078)].

According to the present invention there is also provided a compound of formula III

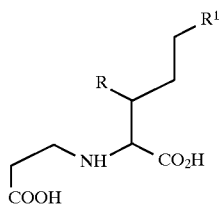

(III)

wherein R is H or OH
and wherein R¹ is

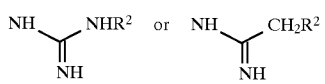

where $R^2$=H or $C_{1-6}$ alkyl.

In a preferred aspect there is provided compound (A):

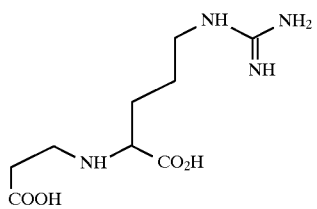

(A)

which is $N^2$-(2-carboxyethyl)-(S)-arginine or derivatives thereof such as activated esters.

Compound A is new and forms a further aspect of the present invention.

Compound A can be prepared according to the following reaction scheme

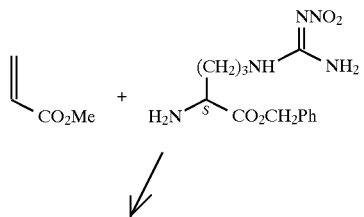

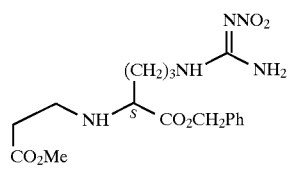

i) OH⁻    ii) H₂/Pd-C

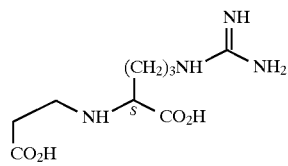

In a further aspect of the invention there is provided a process for preparing B by contacting A or an activated derivative thereof, preferably an ester or CoA thioester, with an enzyme system from Streptomyces, eg. in whole cells or a free enzymatic system.

In a preferred aspect there is provided compound (G):

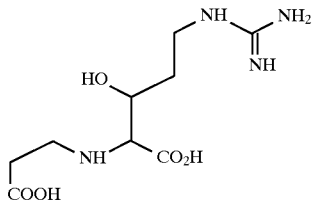

(G)

which is $N^2$-(2-carboxyethyl)-3-hydroxy-(S) arginine or a derivative thereof such as an activated ester.

Compound G is new and forms a further aspect of the present invention.

Compound G can be prepared according to the following reaction scheme:

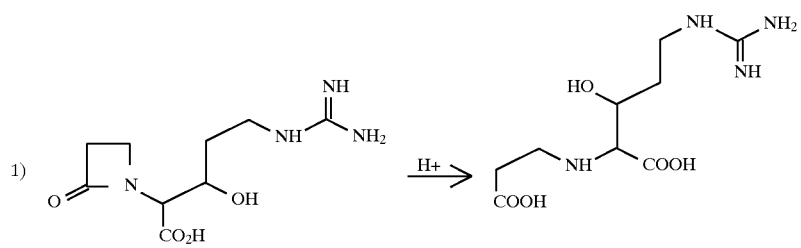

-continued

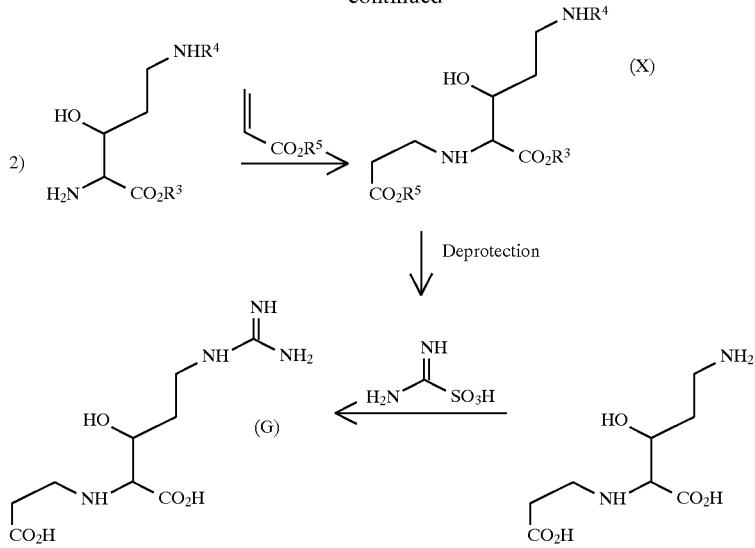

$R^3$, $R^4$ are protecting groups, $R^5$=protecting group or H.

3)

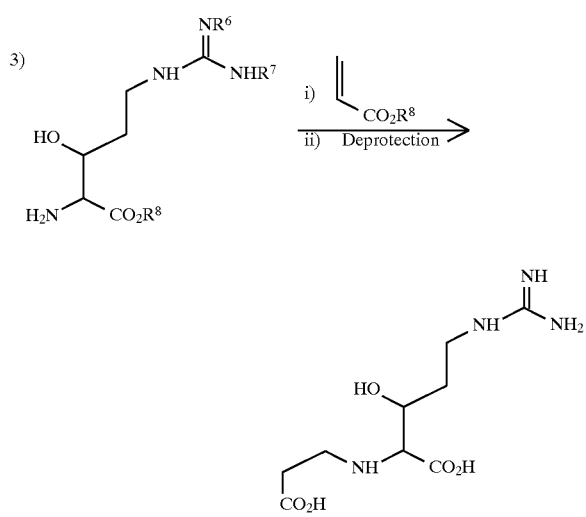

$R^6$, $R^7$, $R^8$ are protecting groups, $R^9$=protecting group or H.

Preparation of compounds of type X are disclosed in K. H. Baggaley, S. W. Elson, N. H. Nicholson and J. T. Sime, J. Chem. Soc. Perkin Trans I 1990, 1521.

In a further aspect of the invention there is a process of producing proclavaminic acid (F) comprising incubating D with CAS.

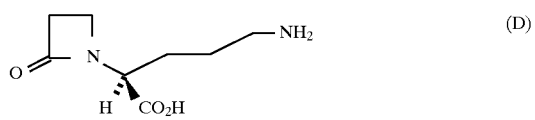

D is (2S)-5-amino-2-(2-oxo-azetidin-1-yl) pentanoic acid [J. Chem. Soc., Perkin Trans.I 1990, 1521].

In a further aspect of the invention there is a process of producing (E) comprising incubating D with CAS.

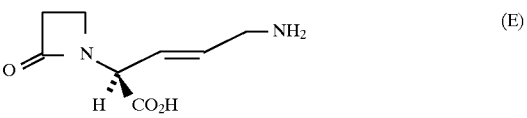

E is a novel compound, E-(2S)-5-amino-2-(2'-oxoazetidin-1'-yl)pent-3-enoic acid, and forms one further aspect of the invention.

The utility of the compounds A, B, C and G or protected forms thereof and their salts resides in their ability to act as intermediates in a process for preparing clavulanic acid as hereinbelow described.

In a preferred aspect the present invention also provides a process for preparing clavulanic acid and other clavam derivatives from any one of S-arginine, A, B, C or G using an enzyme system from Streptomyces, preferably *S. clavuligerus*.

In a further aspect, the present invention provides a method for beta-hydroxylation of compounds of the formula (II), preferably compound B as hereinbefore defined as well as alpha-amino acids or N-acyl derivatives thereof in which the alpha-amino acid substrate carries a basic group in the side chain characterised in that the hydroxylation reaction is carried out by incubating the substrate with CAS. Suitably the reaction is carried out together with requisite cofactors $Fe^{2+}$ and oxygen and co-substrate α-ketoglutarate. Suitable basic groups include amino, guanidino and amidino.

Particular substrates include $N^2$-acyl arginine derivatives such as $N^2$-acetyl arginine and $N^2$-acyl ornithine derivatives such as $N^2$-acetyl ornithine.

The compounds according to the invention may be in the zwitterionic form or in salt form, for example as a metal salt such as, for example, the sodium salt, an acid addition salt, an ammonium salt or a substituted ammonium salt, for example a tertiary amine salt.

Acid addition salts may form at the terminal amino group and may be, for example, salts with inorganic acids such as, for example, hydrochloric acid, hydrobromic acid, orthophosphoric acid or sulphuric acid, or organic acids such as, for example, methanesulphonic acid, toluenesulphonic acid, acetic acid, propionic acid, lactic acid, citric acid, fumaric acid, malic acid, succinic acid, salicylic acid or acetylsalicylic acid.

Metal salts may form at the carboxyl group and may be, for example, aluminium salts and alkali metal and alkline earth metal salts, such as, for example, lithium, sodium, potassium, calcium and magnesium salts.

Substituted ammonium salts may be, for example, those with $C_{1-6}$ alkylamines such as, for example, triethylamine, hydroxy($C_{1-6}$)alkylamines such as, for example, 2-hydroxyethylamine, bis(2-hydroxyethyl)amine or tri(2-hydroxyethyl)amine, cycloalkylamines such as, for example, bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as, for example, pyridine, collidine or quinoline.

It is to be understood that the compounds of the present invention extends to compounds in which one or more of the functional groups present are in protected form Thus where appropriate the carboxy group may be protected, the guanidino, hydroxy or amino group may be protected or both the carboxy and the guanidino, hydroxy or amino group may be protected. All such protected forms of the compounds herein described are embraced by the term 'protected form'. In addition, the term 'protected form' as applied to compounds herein described covers 'masked' intermediates, which may be converted into the final compounds by chemical processes known to be capable of converting one functional group into another (wherein the remainder of the molecule remains substantially unaffected). For example, preferred masked forms of an amine include the corresponding azido and cyano analogues which may be converted into the desired amine by reduction. (It will be appreciated that the corresponding cyario compound has one less carbon atom in the side-chain, excluding the carbon in the-cyano group.)

Suitable ester forming carboxyl-protecting groups include optionally substituted $C_{1-6}$ alkyl, $C_{2-6}$ alkenyl, $C_{2-6}$ alkynyl, $C_{3-7}$ cycloalkyl, aryl, aryl $C_{1-6}$ alkyl, and tri $C_{1-6}$ alkylsilyl groups.

When used herein the term "aryl" includes phenyl and naphthyl, each optionally substituted with up to five fluorine, chlorine, $C_{1-6}$ alkyl, $C_{1-6}$ alkoxy, halo ($C_{1-6}$)alkyl, hydroxy, amino, carboxy, $C_{1-6}$ alkoxycarbonyl, aryloxycarbonyl, $C_{1-6}$ alkoxycarbonyl ($C_{1-6}$)alkyl, nitro, aryloxycarbonyloxy, aryl $C_{1-6}$ alkyloxycarbonyloxy, $C_{1-6}$ alkyloxycmbonyloxy, $C_{1-6}$ alkylcarbonyloxy, arylcarbonyloxy, aryl $C_{1-6}$ alkylcarbonyloxy, or aryl $C_{1-6}$ alkyloxycarbonyl groups.

The term "halogen" refers to fluorine, chlorine, bromine and iodine. The terms halo and halide should be interpreted accordingly.

Some examples of optional substituents in protecting groups mentioned herein as being optionally substituted include up to three groups (which may be the same or different) chosen from halogen, hydroxy, $C_{1-6}$ alkoxy, $C_{1-6}$ alkylthio, cyano, nitro, carboxy, carboxylic acid $C_{1-6}$ alkyl ester, carbamoyl, amino, mono ($C_{1-6}$) alkylamino, and di ($C_{1-6}$) alkylamino.

Particularly suitable ester-forming carboxyl-protecting groups are those which may be removed under conventional conditions. Such groups include $C_{1-6}$ alkyl such as methyl and ethyl, benzyl, p-methoxybenzyl, benzoylmethyl, p-nitrobenzyl, 4pyridylmethyl, 2,2,2-trichloroethyl, 2,2,2-tridbromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, or a silyl, stannyl or phosphorus-containing group.

A carboxyl group may be regenerated from any of the above esters by usual methods appropriate to the particular ester group, for example, acid- and base-catalysed hydrolysis, or by enzymicallycatalysed hydrolysis, or by hydrogenolysis under conditions wherein the remainder of the molecule is substantially unaffected.

A preferred carboxyl protecting group in the compound of the invention or a salt or amino-protected derivative thereof is benzyl.

Suitable protecting groups for the amino group are those which may readily be cleaved. A comprehensive discussion of the ways in which an amino group may be protected and methods for cleaving the resulting protected derivatives are given, for example, in "Protective Groups in Organic Synthesis" by T. W. Greene and P. G. M. Wuts (Wiley-Interscience, New York, 1991).

Suitable examples of amino protecting groups include masking groups as hereinabove discussed; optionally substituted $C_{1-6}$ alkylcarbonyl; arylcarbonyl; aryl $C_{1-6}$ alkylcarbonyl; (heterocyclyl)carbonyl wherein the heterocyclyl group is a 5-or 6-membered aromatic ring containing up to 4 heteroatoms selected from oxygen, nitrogen and sulphur, or a group affording a carbamate such as benzyloxycarbonyl optionally substituted in the phenyl ring by one or two substituents selected from $C_{1-4}$ alkyl, $C_{1-4}$ alkoxy, tifluoromethyl, halogen or nitro; $C_{1-4}$ alkyloxycarbonyl, for example tert-butoxycarbonyl; or $C_{1-4}$ alkyloxycarbonyl optionally substituted in the alkyl group by up to three substituents chosen from $C_{1-4}$ alkoxy, halo or nitro, for example 2,2,2-trichloroethoxycarbonyl or 1-chloroethoxycarbonyl.

Preferred examples of N-protecting groups for the amino group present in the compound of the invention include those conventionally known for amino protection in peptide chemistry, as discussed hereinbelow.

A particularly preferred amino protecting group in the compounds of the present invention or a salt or carboxy-protected derivative thereof is benzyloxycarbonyl.

Suitable guanidino and amidino protecting groups include nitro, benzyloxycarbonyl, adamantyloxycarbonyl, toluenesulphonyl,and 2,2,5,7,8-pentamethyl-chroman-6-sulphonyl.

Desirably the compounds will be in isolated form, free of nucleic acid material. The compounds are suitably, for example, substantially pure, more suitably at least 75% pure and preferably at least 85% pure, for example, 90–100% pure. One preferred isolated form is as the solid form, more preferably as the crystalline form. However, it should be understood that none of the above precludes using the compound in an impure form.

When the compounds of this invention are allowed to crystallise, or are recrystallised, from organic solvents, solvent of crystallisation may be present in the crystalline product. This invention includes within its scope such solvates. Similarly, the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Specific compounds within this invention or a salt or protected form thereof include the following:

(A) $N^2$-(2-carboxyethyl)-S-arginine (B) (2S)-5-guanidino-2-(2-oxo-azetidin-1-yl) pentanoic acid (C) threo-3-hydroxy-5-guanidino-2-(2-oxo-azetidin-1-yl) pentanoic acid, preferably 2S-3R.

(E) E-(2S)-5-amino-2-(2'-oxoazetidin-1'-yl)pent-3-enoic acid (G) $N^2$-(2-carboxyethyl)-3-hydroxy-arginine.

The term 'enzyme system' as used herein denotes either one enzyme or a series of enzymes. Suitably the system includes co-substrates and co-factors where appropriate.

Compounds having asymmetric carbon atoms may exist in stereoisomeric forms. The present invention encompasses all stereoisomers of the compounds of the present invention and the use thereof whether free from other isomers or admixed with other isomers in any proportion, and thus includes, for instance, racemic mixtures of enantiomers. Solvates, especially hydrates, of the compound of the present invention or a salts thereof are also included within the scope of the invention.

The processes of this invention are suitably carried out, for example, in a cell-free system, that is in the absence of living cells. Preferably the enzyme system employed is derived from a microorganism, in particular a species of Streptomyces. Alternatively, the enzyme(s) may be produced by genetic engineering.

If a cell-free system is employed, a cell-free extract is preferably produced by sonication or other disruption of the microorganisms, optionally thereafter removing cell debris, leaving the enzyme system in solution. The enzyme system producing proclavaminic acid (F) or a salt thereof suitably comprises, for example, an amidinohydrolase enzyme.

The enzyme is suitably prepared according to the examples described herein.

In addition to substrate the enzyme reaction mixture may contain one or more other cofactors. Usually those cofactors will include an additional source of manganous ions, ($Mn^{2+}$).

A preferred source of the enzyme is a species of Streptomyces such as, for example, strains of or derived from *S. clavuligerus, S. jumonjinensis, S. katsurahamanus* and *S. lipmanii*. In particular the following strains of these microorganisms are useful: *S. clavuigerus* ATCC 27064, *S. jumonjinensis* ATCC 29864, *S. Katsurahamanus* T-272, *S. lipmanii* NRRL 3584.

A preferred enzyme is derived from *S. clavulis* ATCC 27064.

The enzyme may be prepared by culturing the microorganism in a conventional manner, especially under aerobic conditions in a suitable liquid or semi-solid medium. In general, carbon and nitrogen sources which microorganisms can assimilate and inorganic salt nutrients essential for the growth of the microorganisms are included in the culture medium.

The culture medium should contain a source of metal ions such as, for example, iron. The culture conditions may be a temperature in the range of from 10° C. to 80° C. and pH in the range of from 3 to 10. Preferred conditions are from 20° C. to 30° C. at a pH of from 5 to 9, suitably, for example, about pH 7, for 0.5 to 5 days.

The enzyme may be isolated and used in purified form, partially purified form, as obtained in an impure state, as a filtrate from a disrupted cell preparation, or as a crude cell homogenate.

Most suitably the enzyme is, for example, at least partially purified to remove other enzymes which might catalyse the destruction of the precursor, the enzyme, or the clavam nucleus. The enzyme may be attached to an insoluble polymeric support.

The process of the present invention is generally carried out in aqueous media, the reaction mixture suitably being maintained in the range of from pH 4 to 9, more suitably, for example, from 6.5 to 9.0, preferably about pH 8.5. The pH is suitably controlled, for example, using buffers, such as, for example, 3-(N-morpholino)propanesulphonic acid buffer at pH 7. Alternatively the pH may be controlled by the addition of a suitable acid or base. The temperature of the reaction should be that suitable for the enzyme employed and is generally in the range of from 15° C. to 60° C., preferably about 30° C. The reaction time depends on such factors as concentrations of reactants and cofactors, temperature and pH.

The compound or salt thereof is suitably dissolved, for example, in buffer before mixing with the enzyme. The concentration of precursor solution will depend upon the solubility of the precursor, usually the concentration of the precursor solution is in the range of from 5% w/v to 0.001% w/v. After the reaction is complete, the enzyme may be separated from the reaction mixture and the compound or a salt thereof isolated by conventional methods. The initial purification of the compound or a salt thereof conveniently involves a chromatography step. The compound may be isolated in a form where the carboxyl and/or the amino group present is protected and, if desired, the protecting group(s) may be subsequently removed to generate the compound in a pure form.

Instead of employing a cell-free system, the process of this invention may also be operated using an intact microorganism. The precursor compound or salt thereof is then provided and contacted with the microorganism to produce the compound or salt thereof. The microorganism may be in the form of a growing culture, resting culture, washed mycelium, immobilised cells, or protoplasts.

The compounds of the invention may also be prepared by enzymic synthesis, e.g. a cell free synthesis or by isolation from a suitable strain of a Streptomyces species, for example *S. clavulierus, S. jumoninensis, S. katsurahamanus,* or *S. lipmanii*. Suitably, isolation of the compounds involves disruption of the mycelium and isolation of the compounds from the cell contents. Typically, isolation of the compounds in purified form will involve chromatographic procedures. Alternatively, the compounds may be used in an impure or partially pure form.

It will be understood that a salt of the compounds may be prepared by the methods described above wherein a salt of a starting material is used, or free compounds prepared is subsequently converted into a salt. Also, if desired, a salt of the compounds prepared may be converted into the free unsalified compound or into another salt of the compounds.

The salts of the compounds may be produced, for example, by treating the compounds with the appropriate acid or base. The compounds and salts thereof produced by the above processes, may be recovered by conventional methods.

The compounds possessing two chiral centres may be separated into diastereoisomeric pairs of enantiomers, if so desired, by, for example, fractional crystallisation from a suitable solvent, for example methanol or ethyl acetate or a mixture thereof. The pair of enantiomers or other pairs of enentiomers may be separated into individual stereoisomers by conventional means, for example by the use of an optically active salt as a resolving agent or by stereoselective removal of a protecting group using a suitable enzyme, for example an esterase such as subtilisin. In mixtures of diastereoisomers of the compounds the ratio of diastereoisomers may be changed by treatment with a non-nucleophilic base, for example 1,5-diazabicyclo[4.3.0]non-5-ene.

Suitable optically active compounds which may be used as resolving agents are described in 'Topics in Stereochemistry', Vol. 6, Wiley Interscience, 1971, Allinger, N. L. and Eliel W. L., Eds.

Alternatively, any enantiomer of a the compounds may be obtained by stereospecific synthesis using optically pure starting materials of known configuration.

This invention also extends to the compounds or a salt thereof for use in the synthesis of clavulanic acid.

In a further aspect of the present invention, there is provided a process for the preparation of clavulanic acid or a salt thereof, which process comprises treating a compound according to the present invention or a salt thereof with an enzyme system. There is also provided by the present invention clavulanic acid or a salt thereof whenever prepared by such a process.

Preferably the enzyme system employed is derived from a microorganism, in particular a species of Streptomyces. Suitably the process is carried out in a cell-free system. Suitably the cell-free synthesis of clavulanic acid comprises treating a compound or a salt thereof with an extract of a species of Streptomyces.

Suitably the species of Streptomyces is a clavulanic acid producing species.

The extract from a species of Streptomyces comprises an enzyme system. The cell-free extract is preferably produced by sonication or other disruption of the Streptomyces cells and optionally thereafter removing cell debris leaving the enzyme system in solution or suspension. The enzyme system may be derived from alternative sources; for example the enzyme(s) may suitably be produced by genetic engineering. A preferred enzyme system is derived from a clavulanic acid producing species of Streptomyces such as, for example, clavulanic acid producing strains of *S. clavuligerus*, *S. jumoninensis* and *S. katurahamanus* or strains derived therefrom, for example mutant strains. In particular the following strains of these microorganisms are suitable: *S. clavuligerus* ATCC 27064, *S. jumonjinensis* ATCC 29864 and *S. katsurahamans* T-272.

Instead of employing a cell-free system, the above process may also be operated using an intact micro-organism. The precursor compound or a salt thereof is then contacted with the micro-organism to produce clavulanic acid or a salt thereof. The micro-organism may be in the form of a growing culture, resting culture, washed mycelium, immobilised cells, or protoplasts.

The enzyme system may be prepared by culturing the microorganism in a conventional manner, especially under aerobic conditions in a suitable liquid or semi-solid medium. In general, carbon and nitrogen sources which microorganisms can assimilate, and inorganic salt nutrients normally used to promote the growth of the microorganisms, are included in the culture medium. The culture conditions may be a temperature in the range of from 10° C. to 80° C. and pH in the range of from 3 to 10. Preferred conditions are from 20° C. to 30° C. at pH of from 5 to 9, for example about pH 7, for 0.5 to 5 days. The enzyme system may be isolated and used in purified form, partially purified form, as obtained in an impure state as a filtrate from a disrupted cell preparation or as a crude cell homogenate.

Most suitably the enzyme system is at least partially purified to remove other enzymes which might catalyse the destruction of the precursor, the enzyme(s), or the reaction product. The enzyme(s) may be attached to an insoluble support The process is generally carried out in aqueous media, the reaction mixture being maintained in a range of from pH 4 to 9, more suitably for example 6.5 to 8.5. The pH is suitably controlled using conventional buffers known in the art In one embodiment, for example, 3-(N-morpholino)propanesulphonic acid buffer (pH 7) is used. The temperature of the reaction should be suitable for the enzyme employed and is generally in the range of from 15° C. to 40° C., preferably about 30° C. The reaction time depends on such factors as concentrations of reactants, temperature and pH.

The compound or a salt thereof is for example suitably dissolved in buffer before mixing with the enzyme system; the concentration will depend upon the solubility of the compound or a salt thereof. Suitably the concentration of the solution of compound or a salt thereof may be in the range of 5% w/v to 0.001% w/v. After reaction is complete, the enzyme(s) may be separated from the reaction mixture and the clavulanic acid or a salt thereof may be isolated by conventional methods. The initial purification of the clavulanic acid or a salt thereof conveniently involves a chromatography step.

In another embodiment of this invention there is provided a process for converting the compound or a salt thereof to clavulanic acid or a salt thereof by treatment with an enzyme system as hereinabove described. Suitably the reaction is carried out in a cell-free synthesis without intermediate isolation of the compound or a salt thereof. Alternatively the conversion of the compound into clavulanic acid is carried out directly using an intact micro-organism.

Figure 1:
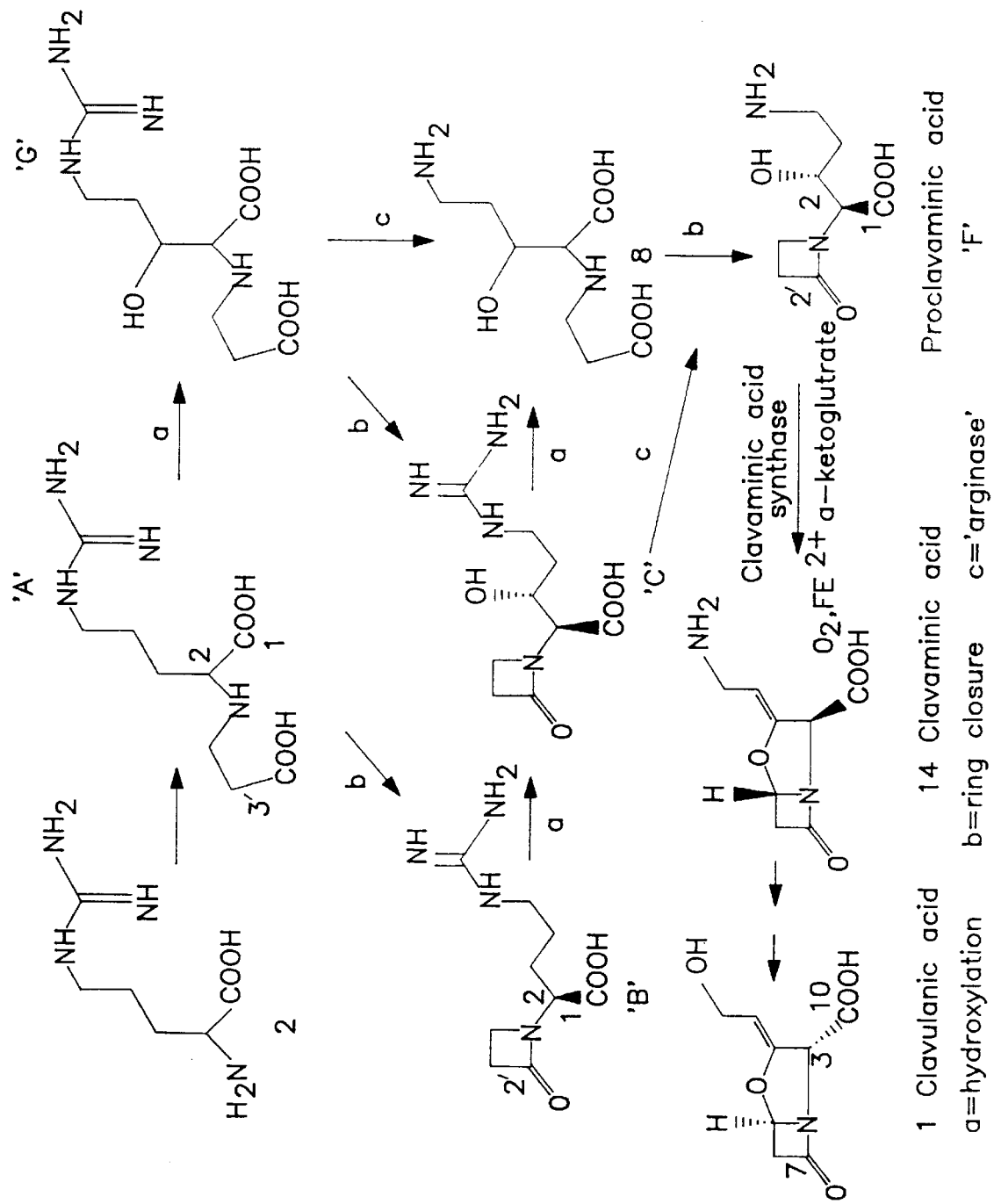
FIG. 1 shows a number of possible biosynthetic sequences prior to proclavaminic acid.

The following Examples illustrate the present invention. All percentages quoted therein are given on a weight basis, and all ratios are given on a volumetric basis.

EXAMPLES

Preparation of Novel Compounds

Compound A $N^2$-(2-Carboxyethyl)arginine dihydrochloride.

Preparation 1

5-Guanidino-2-(2-oxoazetidin-1-yl)pentanoic acid (46 mg, 0.18 mmol) was dissolved in 1M HCl (5 ml) and stirred at room temperature for one hour. The reaction mixture was evaporated to dryness, azeotroped with water and desicated to give a deliquescent white solid, $N^2$-(2-carboxyethyl) arginine dihydrochoride; (Found. C, 31.69; H, 6.57; N, 17.08. $C_9H_{18}N_4O_4$.2HCl.H$_2$O requires C, 32.05; H, 6.58; N, 16.62%.); m/e (FAB,glycerol) MH$^+$ 247 $C_9H_{18}N_4O_4$ requires 247; $v_{max}$ (KBr) 3 410,2 925, 1 725, and 1 661 cm$^{-1}$., δH(250 MHz,D$_2$O) 1.55–1.83 (2H, m), 1.85–2.15 (2H, m) (3-H,4-H), 2.85 (2H, t, J=6.5 Hz, 2'-H ), 3.23 (2H, t, J=6.8 Hz), 3.34 (2H, t, J=6.5 Hz), (5-H and 1'-H), 3.93 (1H, t, J=6.3 Hz, 2-H).

Preparation 2 a) Preparation of $N^2$-(2-carbomethoxyethyl)-N ω-nitro-S-arginine benzyl ester

A mixture of Nω-nitro S-arginine benzyl ester ditosylate (6.56 g, 0.01 mol) (prepared as in H. Otsaka et al Bull. Chem. Soc. Jap. 39 882 1966) triethylamine (13.9 ml, 0.1 mol) and methyl acrylate (9 g, 0.105 mol) in ethanol (100 ml) was stirred at room temperature for 4 days. The solvent wa removed under vacuum, the residue taken up in chloroform and washed with water. The chloroform solution was dried (MgSO$_4$), filtered and evaporated to yield a gum (8.9 g). This material was chromatographed on silica gel using 5% MeOH/CHCl$_3$ as eluant and again eluting with 5–10% n-PrOH/CHCl$_3$ to yield the title compound 2.24 g (60%). $v_{max}$(KBr) 3310, 1738, 1630, 1600 and 1265 cm$^{-1}$. δH (250 MHz, CDCl$_3$), 1.3–1.9 (5H, m), 2.3 (2H, m) 2.7–2.85 (1H, m), 2.85–3.0 (1H, m), 3.2–3.4 (3H, m), 3.69 (3H, s), 5.17 (2H, s), 7.36 (5H, m), 7.6 (2H, s) and 8.75 (1H, s), m/z (NH$_3$ C.I.) (Found MH$^+$ 396 C$_{17}$H$_{25}$N$_5$O$_6$ requires 396)

b) Preparation of N$^2$-(2-carboxyethyl)-S-arginine (Compound A)

A solution of the foregoing methyl benzyl ester (prepared as in a) above) (2.2 g 5.56 mmol), sodium hydroxide (0.45 g 11 mmol) in THF/H$_2$O 1:1 (20 ml) was stirred at room temperature for 4 hours. The pH of the solution was brought to 6 with dil.HCl, the solvents evaporated, then the residue dissolved in H$_2$O/MeOH/AcOH (25 ml:25 ml:5 ml) and hydrogenated over 10% Pd/C (500 mg). The catalyst was filtered off, the solution evaporated to dryness and the residue dissolved in water and freeze dried. Addition of methanol to the residue gave the tide compound A as a white, solid (626.4 mg, 45%) m.p. 260° decomp.(Found: C, 42.33; H, 7.35; N, 20.6, C$_9$H$_{18}$N$_4$O$_4$½H$_2$O requires: C: 42.35, H, 7.5N 21.95%). $v_{max}$(KBr) 2939, 1624, and 1401; δH (250 MHz, D$_2$O) 1.3–1.75 (2H, m), 1.8–2.2 (2H, m), 2.54 (2t, J=6.5 Hz), 3.13–3.28(4H, m) 3.63 (1H, t, J=6.1 Hz); m/z (FAB, thioglycerol) Found: MH$^+$ 247, C$_9$H$_{18}$N$_4$O$_4$ requires 247.

Compound B

5-Guanidino-2-(2-oxoazetidin-2-yl)pentanoic add.

5-Amino-2-(2-oxoazetidin-1-yl)pentanoic acid (310 mg, 1.59 mmol) was dissolved in water (30 ml) and treated with potassium carbonate (240 mg, 1.74 mmol) and aminoiminomethanesulphonic acid (269 mg, 2.17 mmol) and stirred at room temperature for six hours.

The reaction mixture was evaporated to dryness, dissolved. in water (4.5 ml) to which ethanol (30 ml) was added, and the solution was chromatographed rapidly over a column of silica 60 in 15% aqueous ethanol to give 5-guanidino-2-(2-oxoazetidin-1-yl)pentanoic acid (220 mg; 54%), (Found: C, 42.56; H, 7.52; N, 22.15. C$_9$H$_{16}$N$_4$O$_3$. 1.5H$_2$O requires: C, 42.34; H, 7.50; N, 21.95%); $v_{max}$(KBr) 3 423, 1 720, 1 658 and 1 637 cm$^{-1}$; δ$_H$(250 MHz; D$_2$O) 1.45–1.63 (2H, m), 1.63–1.94 (2H, m) (3-H and 4-H), 2.80–3.00 (2H, m, 3'-H), 3.17 (2H, t, J=6.8 Hz, 5-H), 3.26–3.46 (2H, m, 4'-H), 4.03 (1H, dd, J=5.1 and 9.5 Hz, 2-H) and 5-amino-2-(2-oxoazetidin-1-yl)pentanoic acid (90 mg, 29%).

Compound C

3-Hydroxy-5-guanidino-2-(2-oxoazetidin-1-yl)pentanoic acid

Proclavaminic acid (84.5 mg, 0.42 mmol) was treated aminoiminomethane-sulphonic acid in the fashion described above for the preparation 5-guanidino-2-(2-oxoazetidin-1-yl)pentanoic acid (Compound B) to give 3-hydroxy-5-guanidino-2-(2-oxoazetidin-1-yl)pentanoic acid as a white solid (62 mg, 53%), (Found: C, 38.76; H, 6.83; N, 19.54. C$_9$H$_{16}$N$_4$O$_4$. 2H$_2$O requires: C, 38.57; H, 7.19; N, 19.99% (FAB; thioglycerol) MH$^+$ 245, C$_9$H$_{16}$N$_4$O$_4$ requires 245; $v_{max}$(KBr) 3 363, 1 719, 1 673, and 1 600cm$^{-1}$, δH(400 MHz; D$_2$O) 1.73–1.93 (2H, m, 4-H), 3.07(2H, t, J=4.0 Hz, 3'-H), 3.41 (2H, t, J=6.5 Hz, 5-H), 3.42–3.60 (1H, m), 3.60–3.68 (1H, m) 4'-H), 4.12 (1H, d, J=5.4 Hz, 2-H), 4.22 (1H, m, 3-H).

Preparation of (2SR, 3RS)-1,2,3'-[$^{13}$C$_3$]-[N$^2$-(2-carboxyethyl)-3-hydroxy-5-guanidino-pentanoic acid ($^{13}$C-labelled G)

Impure (2SR, 3RS)-1,2,3'-[$^{13}$C$_3$]-3-hydroxy-5-guanidino-(2-oxo-azetidin-1-yl)pentanoic acid (270 mg) was dissolved in 1M HCl (5 ml) and stood at room temperature for 2 hours. The solution was evaporated, dissolved in water (1.5 ml) and applied as a column (3×1.5 cm) of Dowex 50W×8 ion exchange resin (H$^+$ form). The column was washed with water (20 ml) then eluted with ammonium hydroxide (0.4M), collecting 5 ml fractions. Fractions giving a positive Sakaguchi reaction were cooled and freeze-dried to yield the title compound as a hygroscopic solid (99.2 mg). Found C, 36.86; H, 6.04; N, 19.88%. $^{13}$C$_3$C $_6$H$_{18}$N$_4$O$_5$.1.5H$_2$O requires C, 37.36; H, 7.3; N, 19.37%. δH (400 MHz, D$_2$O) 1.5–1.95 (1H, m), 1.95–2.15 (1H, m), 2.65 (2H, q, J=6.1 Hz), 3.1–3.28 (m), 3.3–3.4 (m) and 3.4–3.5 (m) (4H), 3.72 (1H, dd, J=7.5 and 4.5 Hz) and 4.0 (1H, t, J=1 7.5 Hz). δC (100 MHz, D$_2$O) 68.29 (d, J=52 Hz, C-2), 72.52 (d, J=52 Hz, C-1) and 179.64 (s, C-2').

Example 1

Amnidinohydrolase enzyme 1.1 Preparation and reactions of amidinohydrolase enzyme A crude enzyme preparation was prepared from 48 hr re-isolate of S. clavuligerus ATCC 27064 mycelium (see EP-A-0349 121) by centrifugation and ultrasonication in 50 mM Tris buffer pH 7.0.

The hydrolysis of (C) to (F) by the enzyme preparation was quantitative with the production of one equivalent of urea.

The enzyme preparation is incubated with 5 mM Tris, 50 μM MnCl$_2$, 250 μg/ml compound B or C and 5 mM acetohydroxamic acid. The acetohydroxamic acid is included to inhibit urease activity within the extract The mixture is incubated at pH 8.5 at 28° C. for 15 minutes or longer.

The reaction was stopped and the urea produced measured using the 'Sigma' kit 535B. The two compounds C and B were incubated (28° C.) individually with the enzyme preparation and their loss,if any, monitored by hplc.

The derivatives C and B were hydrolysed to F and D respectively and the reaction was enzyme mediated.

The rate of hydrolysis of C was found to be significantly faster (>100) than that of for B as measured by hplc and the production of proclavaminic acid (F) and dehydroxyproclavaminic acid (D).

The hydrolysis of C to F was quantitative with the production of one equivalent of urea The hydrolysis of B was not followed to completion but urea production was equivalent to the amount of D generated.

Experiments to optimise the conditions also revealed the following.

a) the ability to convert a compound of the formula C or a salt thereof as hereinabove defined into proclavanunic acid or a salt thereof as hereinabove defined;

b) the enzyme activity is enhanced in the presence of Mn$^{2+}$, with an optimum Mn$^{2+}$ concentration of around 50 μM.

c) a buffer pH profile reveals that phosphate and borate based buffers inhibit enzyme activity when compared to TRIS, carbonate/bicarbonate or glycine buffers d) the enzyme activity appears to be enhanced the more basic the buffer is towards pH 9.0. However stability studies of compound C at various buffer pH's showed that the compound is unstable at and above pH 9.0. The maximal rate of enzymic conversion of C to proclavaminic acid occurred in 50 mM TRIS at pH 8.5.

e) adding organic solvents (eg. methanol, acetonitrile) to stop the enzyme reaction was found to interfere with either the urea or hplc assaay. Therefore reactions were stopped by placing the samples in an acetone/cardice (−70° C.) bath and then immediate transfer to −70° C. freezer until just before assay. The enzyme activity was not stopped by freezing at −20° C.

This enzyme does not cleave arginine (at a rate that can be detected) but was found to cleave (2S)-5-guanidino-2-(2-oxo-azetidin-1-yl)pentanoic acid.

Arginase activity is separated from amidinohydrolase activity during the purification (under 1.2 below).

1.2 Amidinohydrolase purification

Experimental

The *S. clavuligerus* cells were grown in standard carbohydrate medium, harvested and then sonicated in the following buffer: 50 mM Tris-acetate (Tris-Ac), 50 $\mu$M MnCl$_2$, 1 mM phenylmethylsulphonyl fluoride (PMSF), 1 mM dithiothreitol (DTT), pH 8.0. After extensive dialysis against the above buffer, the sonicate was fractionated using ion-exchange chromatography (DEAE-Sepharose Fast Flow, Pharmacia) with 0–1M NaCl gradient elution. Enzymic urea production was assayed using Sigma urea kit 535B, with the addition of 5 mM acetohydroxamic acid to inhibit any urease activity. Each fraction was assayed twice with S-arginine and compound C as respective substrates, to determine arginase and amidinohydrolase activity. Both activities were found to elute at approximately 0.5M NaCl (top of column) and the specific activities were increased 1.9-fold and 2.4-fold respectively.

The active fractions from this procedure were dialysed extensively against 50 mM Tris-Ac/0.5M NaCl/pH 8.0 before being applied to a metal chelate affinity column. This was prepared using iminodiacetic acid—agarose (Sigma) loaded to 75% capacity with CuSO$_4$ and then equilibrated in the above buffer. The column was eluted with a 0–200 mM glycine gradient, giving a sharp peak of amidino-hydrolase activity. This peak also exhibited arginase activity, although only weakly.

The active fractions were pooled and desalted on a Pharmacia PD10 column, before loading onto a lysine-agarose affinity column. Lysine is known to inhibit many arginases—therefore was predicted to be a useful affinity ligand. However, the amidinohydrolase activity was not retained by the column. (Arginase activity was lost subsequent to this column, possibly due to tight binding to the column). An SDS-PAGE analysis of the wash fraction, and eluates from the lys-agarose column showed a prominent band at 33 kD in the wash fraction. This is in the range of most known arginases. However, in order to determine whether amidinohydrolase and arginase are the same enzyme, further purification was required.

This was achieved using HPLC gel filtration with a TSK G3000 SW XL column in 50 mM Tris-Ac/50 $\mu$M MnCl$_2$ pH 7.2 at a flow rate of 0.2 ml min$^{-1}$. The wash fraction from the lysine-agarose column was freeze-dried and resuspended in a small volume of buffer prior to injection onto the column. Fractions were collected and assayed for amidinohydrolase and arginase activity. All of the amidinohydrolase activity was present in one fraction, but no arginase activity was detected in any of the fractions, after 6 hours reaction the amidinohydrolase fraction still had no detectable arginase activity.

Calibration of the gel filtration column with protein standards prior to use allows an estimate to be made of the $M_r$ of native amidinohydrolase. This is calculated at 350+/−50 kD. This is approximately 10-fold greater than the sub-unit Mr by SDS-PAGE—indicating that the non-denatured protein exists in a multimeric state.

SDS-PAGE analysis of the fractions showed that the amidinohydrolase-containing fraction contained one prominent band at 33 kd).

A Western blot from active samples was sequenced by standard protein sequencing techniques and the sequence obtained is shown below:

Protein sequence: IDSHVSPRYAQIPTFM

The predicted amino acid sequence of the open reading frame (ORF) found by sequencing pBROC 44 (see EP-A-0 349 121) was compared to the N-terminal sequence obtained above and was as follows:

Gene sequence (predicted amino acid sequence):
MER/IDSHVSPRYAQIPTFM

There is a perfect match (16/16) when the sequences are aligned. The absence of the first 3 amino acids from the gene sequence in the native protein indicates that post translational modification has taken place.

Example 2

Clavaminic acid synthase 2.1 Clavamininc acid synthase purification

Clavaminic acid synthase (CAS) was purified from *S. clavuligerus* using the method described in EP A 0213 914. Freeze-dried partially purified enzyme (250 mg) was loaded onto a DEAE Sepharose CL-6B (Pharmacia, Uppsala, Sweden) column (30×2.4 cm), washed with 100 ml of 50 mM tris buffer pH 7.0 and eluted with a gradient of 50 to 500 mM tris buffer pH 7.0. CAS positive fractions were pooled and brought to 80% saturation with solid ammonium sulphate. The suspension was kept on ice for 1 hour and centrifuged at 24,000×g for 60 minutes. The precipitate was resuspended in 1 ml of 50 mM tris buffer pH 7.0 plus 0.5 ml 30% sucrose solution (made up in the same buffer) and loaded onto a Sephadex G75 superfine (Pharmacia) column (63.5×3.5cm) which was eluted with 50 mM tris buffer. CAS positive fractions were pooled, brought to 80 percent saturation with solid ammonium sulphate and the resulting precipitate was removed by centrifugation and stored at −20° C. At this stage the CAS enzyme produced a single band corresponding to a molecular weight of approximately 48,000 daltons when examined by sodium dodecyl sulphate polyacrylamide gel electrophoresis. The isoelectric point was determined by isoelectric focusing and gave a value of pI=5.65.

The purified enzyme was assayed for conversion of B to C using the following assay.

2.2 Clavaminic acid synthase hydroxylation assay

All reagents were made up in 50 mM Tris, 10 mM MgCl$_2$ and 10 mM KCl, adding 5M HCl to pH 75 unless otherwise specified. For 100 ml required Tris (0.606 g) MgCl$_2$ (0.203 g), KCl (0.074 g) . The same buffer as that used for the enzyme purifiction was used if possible. The following solutions were required; the cofactor FeSO$_4$10 mM in H$_2$O (2.78 mg per ml); B 100 mM in H$_2$O (20 mg per ml); dithiothreitol (DTT) 10 mM (1.5 mg per ml) and the co-substrate α-ketoglutarate 50 mM (9.5 mg per ml of disodium salt).

A mixture of the foregoing solutions was made and 40 $\mu$l of the resulting solution transferred into a 1.5 ml eppendorf tube and then treated with 60 $\mu$l of protein extract to initiate the reaction. The reaction was incubated at ambient temperature for 5 minutes in the presence of oxygen without shaking, before closing the lids of the tubes. The reaction mixture was quenched by flash heating in a 60 w microwave oven for 15 seconds on power 4. At protein concentrations greater than 1–2 mg per ml a precipitate forms ie the solution goes cloudy. The sample was spun at 13,000 rpm for 10 seconds in a microfuge and the samples stored on dry ice. A 25 microlitre aliquot was injected onto a ODS column (250×4.6 mm) equilibrated in milli Q H2) at 1 ml per min, 0.2 AUFS, lambda=218 nm, 1 cm per min. The product C eluted at about 4.5 minutes and the substrate B at about 8 minutes.

2.3 Incubation of compounds with CAS and recombinant CAS

General Procedure

'CAS' refers to clavaminic acid synthase prepared from a normal clavulanic acid producing strain of *Streptomyces clavuligerus* and 'recombinant CAS' refers to clavaminic acid synthase prepared for example according to the methods in EP349121 (Beecham Group plc).

When isolation of the reaction products was required, CAS (or recombinant CAS) was exchanged into 10mM ammonium bicarbonate buffer combining, 10 mM $MgCl_2$, 10 mM KCl and 1 mM dithiothreitol (DTT), pH 7.5 using either PD-10 or NAP-5 G-25 sephadex gel filtration columns. For the PD-10 column, 2 ml of enzyme solution was loaded onto a column equilibrated with buffer and eluted with 3.5 ml of buffer. For the NAP-5 column 0.5 ml of enzyme was loaded and the column eluted with 1 ml of the same buffer.

Enzyme solution (1.2 ml) was mixed in a 10 ml glass vial with 200 $\mu$l of 10 mM iron (II) sulphate, 200 $\mu$l of 10 mM DTT and 200 $\mu$l of 50 mM $\alpha$-ketoglutarate (made up in 10 mM $NH_4HCO_3$. 10 mM $MgCl_2$, 10 mM KCl, 1 mM DTT, (pH 7.5). The reaction was initiated by addition of 200$\mu$l of substrate (10 mg $ml^{-1}$ aqueous solution unless otherwise stated). The mixture was incubated at 27° C. and 250 r.p.m in a New Brunswick Scientific G24 environmental incubator shaker. After 20 min further 50 $\mu$l aliquots of DTT and iron (II) sulphate stock solutions were added. The reaction was quenched after a total of 45 min by the addition of 5 ml of acetone and the protein removed by subjecting to 25.000×g for 2 min (14,000 r.p.m.) in a Beckman JA-20 centrifuge rotor at 4° C. The supernatant was then transferred into a 10 ml pear-shaped flask and the acetone removed in vacuo on a rotary evaporator. Care was taken to maintain in the incubation mixture on dry ice between manipulations after centrifugation to avoid decomposition of possible labile products. The residual aqueous liquid was titrated with 4–5 drops of 1% (v/v) aqueous formic acid in water to approximately pH 5.0 and freeze-dried for at least 5 hours to remove water and remaining traces of acetone. Crude mixtures were routinely analysed by 500 MHz $^1$H NMR before isolation of the products by HPLC. In the following experiments, the extent of the conversion of the substrates is based on the integration of the appropriate peaks in the 500 $^1$H MHz NMR spectrum. The yield refers to purified products, unless otherwise stated.

Incubation of (2S)-5-amino-2-(2-oxoazetidin-1-yl) pentanoic acid (D)

Compound D was incubated with CAS (1.2 mg, 0.34 IU $mg^{-1}$) according to the standard protocol described above. A ca. 7% conversion to E-(2S)-5-amino-2-(2'-oxoazetidin-1'-yl)pent-3-enoic acid (E) was observed (as judged by the integration of the 500 MHz $^1$H NMR spectrum) HPLC purification [ODS column (250×7 mm) equilibrated in 25 mM $NH_4HCO_3$ at 1.5 ml $min^{-1}$] led to the isolation of E (96 $\mu$g) with a retention volume of 9.15 ml: $\delta$H (500 MHz $D_2O$) 2.95–3.0 (2H, m, H-3'), 3.4–3.5 (2H, m, H-4'), 3.5–3.6 (2H, m, H-5), 5.8–5.9 (1H, m, H-4) and 5.9–6.0(1H, m, H-3). A 2D COSY correlation spectrum was consistent with the proposed structure of E and indicated a signal at ca 4.6 ppm under the residual HOD peak. m/z (electrospray) =185 ($MH^+$, 100%)

Compound D was incubated with crude recombinant CAS (6 mg, 0.034 IU $mg^{-1}$) according to the standard protocol. A ca. 30% conversion to E and <5% conversion to F was observed (as judged by the integration of the 500 MHz $^1$H NMR spectrum). HPLC purification [ODS (250×7 mm), 25 mM $NH_4HCO_3$, 1.5 ml $min^{-1}$] led to the isolation of E (200 $\mu$g) with a retention volume of 9.15 ml and F (<<5 $\mu$g) with a retention volume 6.9 ml. The spectroscopic data for E was consistent with that obtained from the incubation with partially purified CAS. It was not possible to completely assign the $^1$H NMR spectrum (500 MHz) of F. but the resonances were consistent with the proposed structure. m/z (electrospray)=203 ($MH^+$, 100%). For threo-5-amino-3-hydroxy-2-(2-oxoazetidin-1-yl)pentanoic acid F m/z (electrospray)=203 ($MH^+$, 100%). HPLC analysis of the crude incubation mixture [ODS column (250×4.6 rm), 25 mM $NH_4HCO_3$, 1 ml $min^{-1}$] showed that F had an identical retention volume to authentic proclavaminic acid F (3.1 ml) when the two samples were mixed, while F was cleanly separated from synthetic erythro-5-amino-3-hydroxy-2-(2-oxoazetin-1-yl)pentanoic (i.e. erythro-proclavaminic acid) (retention volume 3.4 ml) when the two samples were mixed.

Incubation of (2S)-5-guanidino-2-(2-oxoazetidin-1-yl) pentanoic acid (B)

Compound B was incubated with partially purified CAS (2 mg, 0.3 IU $mg^{-1}$) according to the standard protocol. A >85% conversion to threo-5-guanidino-3-hydroxy-2-(2-oxoazetin-1-yl) pentanoic acid C was observed (as judged by the integration of the 500 MHz $^1$H NMR spectrum). HPLC purification [ODS (250×4.6 mm), $H_2O$, 1 ml $min^{-1}$] led to the isolation of (C) (340 $\mu$g) with a retention volume of 7.5 ml $\delta$H(500 MHz $D_2O$) 1.7–1.8 (1H, m, H-4), 1.8–1.9 (1H, m, H-4), 30 (2H, t, J=4 Hz, H-3'), 3.36 (2H, t, J=7 Hz, H-5) 3.5–3.55 (1H, m, H-4'), 3.59–3.61 (1 H, m, H-4'), 4.1(1H, d, J=5.5 Hz, H-2) and 4.15–4.2 (1H, m, H-3). A 2D COSY correlation spectrum was consistent with the proposed structure of C m/z (electrospray)=245 ($MH^+$, 100%). No residual B was recovered from this reaction.

Compound B was incubated with crude recombinant CAS (5.5 mg, 0.014 IU $mg^{-1}$) according to the standard protocol. A >85% conversion to C was observed (as judged by the integration of the 500 MHz $^1$H NMR spectrum). HPLC purification [ODS (250×4.6 mm), $H_2O$, 1 ml $min^{-1}$] led to the isolation of C (369 $\mu$g) with a retention volume of 7.5 ml. The spectroscopic data for C was consistent with that C from the incubation with partially purified CAS.

Compound B was incubated with purified recombinant CAS (0.18 mg, 0.37 IU $mg^{-1}$) according to the standard protocol. A >85% conversion to C was observed (as judged by the integration of the 500 MHz $^1$H NMR spectrum). HPLC purification [ODS (250×4.6 mm), $H_2O$, 1 ml $min^-1$] led to the isolation of C (350 $\mu$g) with a retention volume of 7.5 ml. The spectroscopic data for C were consistent with that obtained for C from the incubation with partially purified CAS.

Incubation of $N^2$-acetyl-L-ornithine $N^2$-acetyl-L-rnithine was incubated with crude recombinant CAS (6 mg, 0.035 IU $mg^{-1}$) according to the standard protocol. A ca. 17% conversion to (2S)-2-acetamido-5-amino-3-hydroxypentanoic acid (X) and a ca. 5% conversion to E-(2S)-5-amnino-2-acetamidopent-3,4-enoic acid (Y) was observed (as judged by the integration of the 500 MHz $^1$H NMR spectrum). HPLC purification [bondapak amine (250×7 mm), ODS guard column 0.015M $HCO_2H$, 2 ml $min^-1$] led to the isolation of Y (30 $\mu$g) with a retention volume of 9.4–10.0 ml. Further HPLC purification of the fraction between 8–9 ml [ODS (250×4.6 mm), 0.05% aqueous HCO$_2$H, 1 ml min$^{-1}$] led to the isolation of X (99 μg) with a retention volume of 5.5–9.0 ml.

For E-(2S)-5-amino-2-acetamidopent-3,4-enoate (Y), δH($^{500}$ MHz D$_2$O) 2.0 (3H, s, CH$_3$-), 2.33 (2H, d, J=5 Hz, H-5) 3.55 (1H, m, H-2), 5.65–5.75 (1 H, m, H-4) and 5.9–6.0 (1H, m, H-3). A 2D COSY correlation spectrum was consistent with the connectivities of X. Homonuclear decoupling experiments showed J=3 H, 4H=15.2 Hz, indicating the double bond has E stereochemistry. m/z (electrospray) =173 (MH$^+$, 100%).

For (2S)-2-acetamido-5-amino-3-hydroxypentanoic acid X) δH(500 MHz D$_2$O) 1.75–1.85 (2H, m, H-4), 2.1 (3H, s, CH$_3$-) 3.15 (2H, t, J=5 Hz, H-5), 4.2–4.25 (1H, m, H-3), 4.30 (1H, d, J=3.5 Hz, H-2). A 2D COSY correlation spectrum was consistent with the connectivities of Y. m/z (electrospray)=191 (MH$^+$, 100%).

Incubation of N$^2$-acetyl-L-arginine

N$^2$-acetyl-L-arginine was incubated with crude recombinant CAS (6 mg, 0.035 IU mg$^{-1}$) according to the standard protocol. A >85% conversion to (2S)-2-acetamido-5-guanidino-3-hydroxy-pentanoic acid (K) was observed (as judged by the integration of the 500 MHz $^1$H NMR spectrum). HPLC purification [ODS (250×4.6 mm) H$_2$O. 1 ml min$^{-1}$] led to the isolation of K (320 mg) with a retention volume of 4.5 ml. δH (500 MHz, D$_2$O) 1.8–2.0 (2H. m. H-4), 2.1 (3H. s, CH$_3$-) 3.15 (2H, m, H-5), 4.20–4.22 (1H, m. H-3) and 4.25 (1H, d, J=3.5 Hz. H-2). A 2D COSY correlation spectrum was consistent with the connectivities of (K); m/z (electrospray)=233 (MH$^+$, 100%).

Incubation of N-α-acetyl-D-arginine with CAS led to little if (<5%) any production of hydroxylated products. This indicates that CAS converts substrates with (2S) stereochemistry. No conversion of N-α-benzoyl-L-arginine was observed when it was incubated with CAS. These results show that CAS is able to oxidise simple derivatives of omnithine and arginine at unactivated positions.

Studies of the stereospecificity of Clavaminic Acid Synthase catalysed Reactions Incubation of (2S, 3S-5-guanidino-2,3-[$^2$H$_2$]-2-(2-oxoazetidin-1yl) pentanoic acid and (2S, 3R)-5-guanidino-3-[$^2$H]-2-(2-oxoazetidin-1-yl) -pentanoic acid with clavaminic acid synthase resulted in highly stereospecific hydroxylation at C-3, with removal of the pro-R proton or deutron respectively These results indicate that the hydroxylation of B as catalysed by CAS proceeds predominantly with retention of configuration at C-3

Example 3

EXPERIMENTS 3.1 Experiment 1 Demonstration of arginine as a precursor of clavulanic acid $^{14}$C-arginine was fed to two mutant cultures of S. clavuligerus known to be blocked at ornithine transcarbamoylase and argininosuccinate synthetase respectively (these being enzymes which are involved in the conversion of ornithine to arginine). Label was incorporated into clavulanic acid.

When $^{14}$C-ornithine label was similarly fed to the two mutant cultures, no label was incorporated into clavulanic acid. In the following discussion letters and numbers in bold type refer to FIGS. 1 and 2.

3.2 Experiment 2—Two novel arginine derivatives (A) and (G)

Experiment 1 provides evidence to show that arginine is the amino acid which is processed into the clavulanic acid biosynthetic pathway. The next known intermediate on the pathway is the monocyclic β-lactam proclavaminic acid. [1] Hence a β-lactam must be elaborated onto the N$^2$ position of the arginine carbon skeleton. a hydroxyl group introduced at C-3 and the N$^5$ guanidino function hydrolysed.

The monocyclic β-lactams (B) and (C) were made by reaction of the parent amines. proclavaminic acid (2)[1] and dehydroxyproclavaminic acid[1] respectively with aminoiminomethanesulphonic acid.[2] The β-amino acid 2S-(A) was obtained by the route shown below and the βamino acid (G) by acidic hydrolysis of the β-lactam (C).

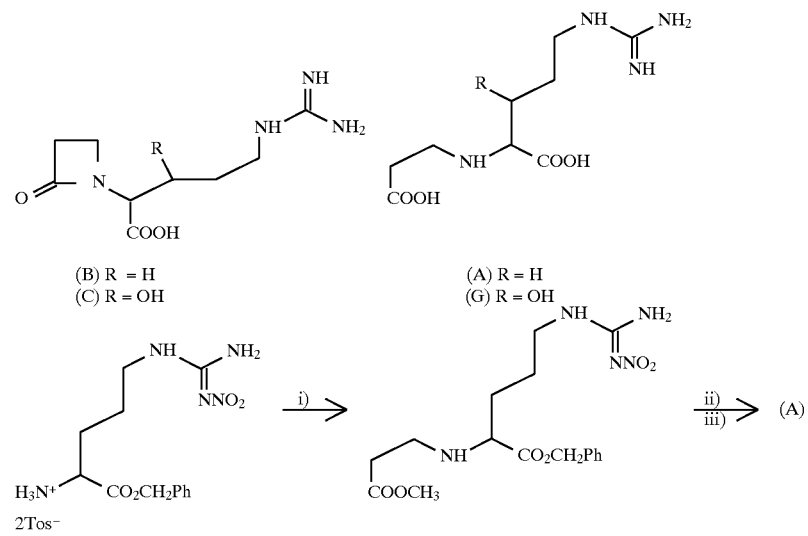

Reagents and conditions: i. Et$_3$N/methyl acrylate; ii. NaOH/THF:H$_2$O (1:1); iii. H$_2$,Pd-C (10%)

None of these putative metabolites were readily detectable in culture supernatant from *S. cavuligerus*. Therefore mutants of *S. clavuligerus* blocked in the production of proclavaminic and hence clavulanic acid were examined Some of these mutants accumulated compounds containing an amine group as shown by derivatisation with phenyhsocyanate.[3] A selection of such mutants were fermented and the culture broths screened for the presence of compounds bering guanidino groups by the Sakaguchi colour reaction.[4] The mutant strain *S. clavuligerus* dclH 65 gave a good response to the colour test. Therefore the culture filtrate was fractionated using Dowex-50, Pharmacia HR5/5 Mono S and Partisil 10SCX cation exchange matrices, the purification of guanidino containing materials being followed by a modified Sakaguchi test procedure (The intensity of the colour formed in the Sakaguchi reaction was measured at 515 nm).

Two compounds were isolated in the approximate ratio 10:1 and by comparison of their spectroscopic properties ( $^1$H n.m.r and fa.b./m.s. for both compounds and $^{13}$C for the major component) with those of the compounds prepared as speculative intermediates, the structures were assigned as (A) and (G) (major to minor).

Since the chromatographic purification process of the *S. clavuligerus* dclH 65 culture broth involved acidic media, there was a possibility that (A) and (G) were ring-opened artifacts of the corresponding β-lactam derivatives (B) and (C), although analytical h.p.l.c. of fresh culture filtrate did not show the presence of ring closed materials. Therefore,a further fractionation of culture broth was carried out maintaining near neutral conditions to avoid hydrolysis of any β-lactam compounds. Fresh culture filtrates of dclH65 were centrifuged, freeze dried, treated with ethanol/water (1:1), to remove high molecular weight compounds and the soluble fraction concentrated. The concentrate was then chromatogaphed over Amberlite IRA68 anion exchange resin, Sephadex Biogel P2 and silica gel whilst maintaining the pH of eluates between 4 and 7.5. Sakaguchi-positive materials were collected at each stage. The major Sakaguchi-positive material was isolated and analysed by $^1$H-n.m.r., i.r., c.d, and mass spectroscopy. These data confirmed the structural assignment of the major product as SEA). The minor Sakaguchi-positive compound was not present in sufficient quantity for isolation but a material was detected which co-eluted with synthetic (G) on h.p.l.c. and capillary zone electrophoresis.

Conclusion

Two novel arginine derivatives, $N^2$-(2-carboxyethyl)-arginine (A) and $N^2$-(2-carboxyethyl)-3-hydroxy-arginine (G), are produced by a mutant of *Streptomyces clavuligerus* dclH65 which is blocked in clavulanic acid biosynthesis. These compounds may be useful in clavulanic acid synthesis.

Further experimental data on the role of these compounds as intermediates of the clavulanic acid biosynthetic pathway are given in Experiment 3.3.

Figure 2:
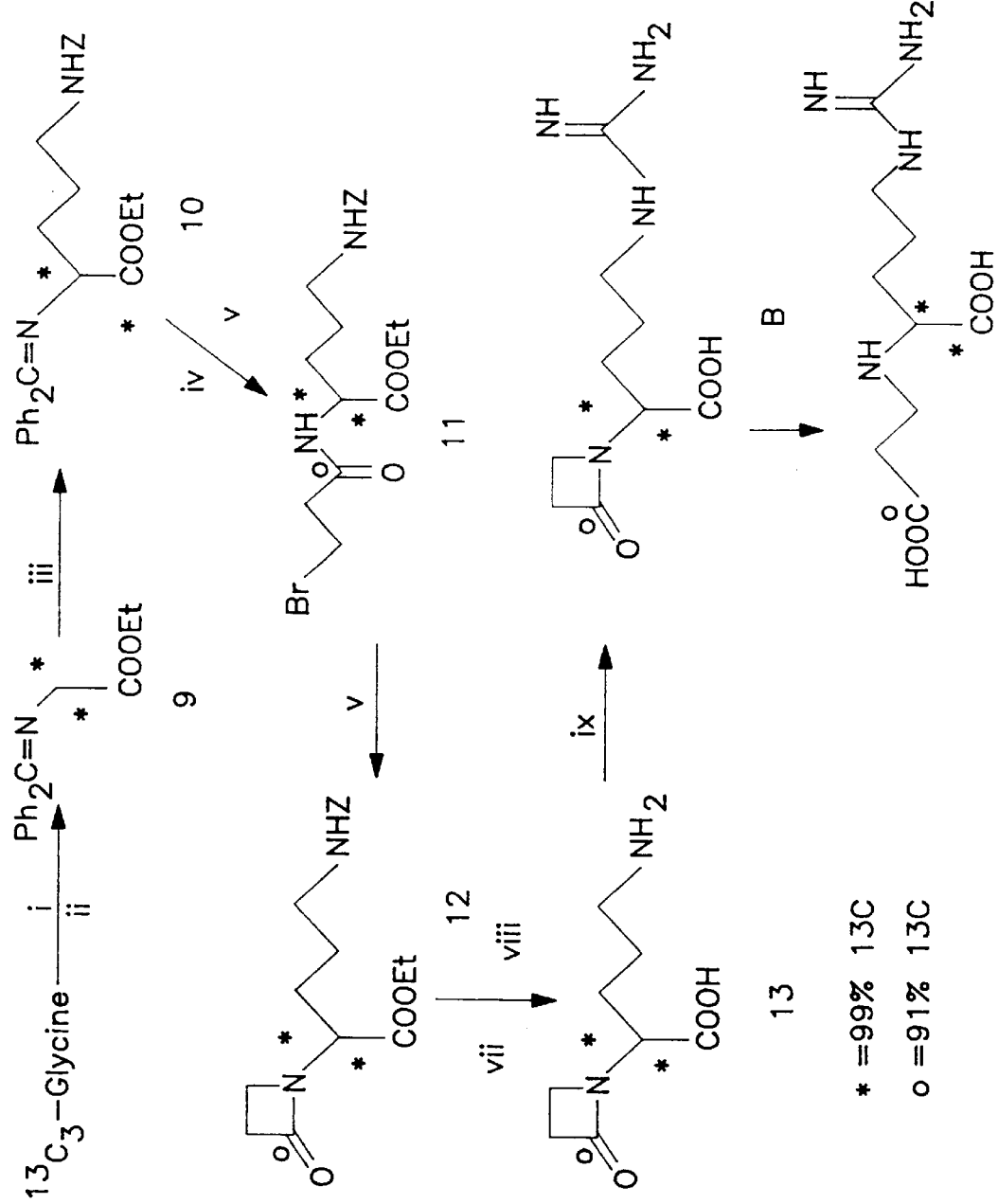
FIG. 2 shows the synthesis of $[1,2,3'-^{13}C_3]$-(A) and $[1,2,2'-^{13}C_3]$-(B). The reagents and conditions are as follows: Z=PhCH$_2$OCO—: I, EtOH, HCl, Δ; ii, PhCHO, MgSO$_4$, Et$_3$N; iii, LDA, HMPA, ICH$_2$CH$_2$NHZ, iv, 1M HCl; v, NaOH, BrCH$_2$CH$_2$$^{13}$COCl; vi, powdered KOH, TBAB, H$_2$O, sonicate; vii, Na$_2$CO$_3$, 40% aq. EtOH; viii, H$_2$, Pd-C (10%); ix, K$_2$CO$_3$, aminoiminomethanesulphonic acid; x, 1M HCl.

3.3 —Experiment 3 Labelling experiments on the role of (A), (B),(C),(G) and (8) as intermediates of the clavulanic acid biosynthesis A number of possible biosynthetic sequences prior to proclavaminic acid are shown in FIG. 1. Commencing with (A) at least three biochemical steps are required to generate proclavaminic acid, i.e. the introduction of a hydroxyl function (step a), formation of the β-lactam ring ( step b ), and hydrolysis of the guanidino group to an amino group (step c). To determine which, if any, of compounds (A,(G) (B), (C) and (8) actually lie on the pathway they were synthesised triply labelled with $^{13}$C for feeding experiments. In each case the five carbon chain was labelled in the 1 and 2-positions (99% $^{13}$C ) and also the carbonyl group of the three carbon unit (91% $^{13}$C). This labelling strategy was adopted since it was known[5] that spin-spin coupling, between carbons 7, 3 and 10 of clavulanic acid, would be observed in the $^{13}$C-n.m.r. spectrum if incorporation of all three labelled carbons occurred without bond breakage.

Treatment of DL-threo-[1,2,2'-$^{13}C_3$]-proclavaminicacid[5], with aminoiminomethanesulphonic acid[2] yielded [1,2,2'$^{13}C_3$]-(C) which on acid hydrolysis yielded [1,2,3'-$^{13}C_3$]-(G). Acid hydrolysis of [1,2,2'-$^{13}C_3$]-(F) gave [1,2,3-$^{13}C_3$]-(8). The synthesis of [1,2,3'-$^{13}C_3$]-(A) and [1,2,2'-$^{13}C_3$]-(B) as according to FIG. 2 In FIG. 2 the reagents and conditions are as follows: Z=PhCH$_2$OCO—: i, EtOH, HCl, Δ; ii, PhCHO, MgSO$_4$, Et$_3$N; LDA, HMPA, ICH$_2$CH$_2$CH$_2$NHZ, iv, 1M HCl; v, NaOH, BrCH$_2$C H$_2$$^{13}$COCl; vi, powdered KOH, TBAB, H$_2$O, sonicate; vii, Na$_2$CO$_3$, 40% aq. EtOH;[16] viii, H$_2$, Pd-C (10%); ix, K$_2$CO$_3$, aminoiminomethanesulphonic acid; x, 1M HCl.

Following the method of Stork et al [6] $^{13}C_2$-glycine (99% 1,2-$^{13}$C) was elaborated into the protected [1,2-$^{13}C_2$]-ornithine derivative (10) via the benzylidene glycine ester (9). Mild acid hydrolysis of (10) yielded the amino ester which was acylated with [1-$^{13}$C]-3-bromopropionyl chloride (91% 1$^3$C )[5] to yield (11). Base treatment of (11) gave the β-lactam (12). Cleavage of the carboxy and amino protecting groups afforded the [1,2,2'-$^{13}C_3$]-(D)[1] which was converted to the target guanidino acid [1,2,2'-$^{13}C_3$]-(B) with aminoiminomethanesulphonic acid.[2] Acid treatment of [1,2,2'-$^{13}C_3$]-(B) yielded [1,2,3'-$^{13}C_3$]-(A). The average yield of the steps in this reaction scheme was 87%.

The five racemic $^{13}C_3$-labelled compounds (A), (G), (B), (C) and (8) were each fed to an *S. clavuligerus* ATCC 27064 fermentation, in the clavulanic acid production phase, and the clavulanic acid samples produced were isolated as the benzyl ester. The levels of incorporation of the administered compounds were determined by $^{13}$C-n.m r and after silylation, gc/m.s. of the 9O-silylated derivatives. The observed $^{13}$C-incorporations are summarised in Table 1 below.

TABLE 1

Summary of $^{13}$C-labelled precursor feeding experiments.

| Precursor | % Incorporation ($^{13}$C-n.m.r.) | % Incorporation (Mass spec.) |
|---|---|---|
| (A) | 1.1% | 1.3% |
| (G) | ND | ND |
| (B) | 11.8% | 12.0% |
| (C) | 5.1% | 5.3% |
| (8) | ND | ND |

ND = No enrichment detected at any carbon centre. Calculations based on one enantiomer being utilised.

Figure 3:
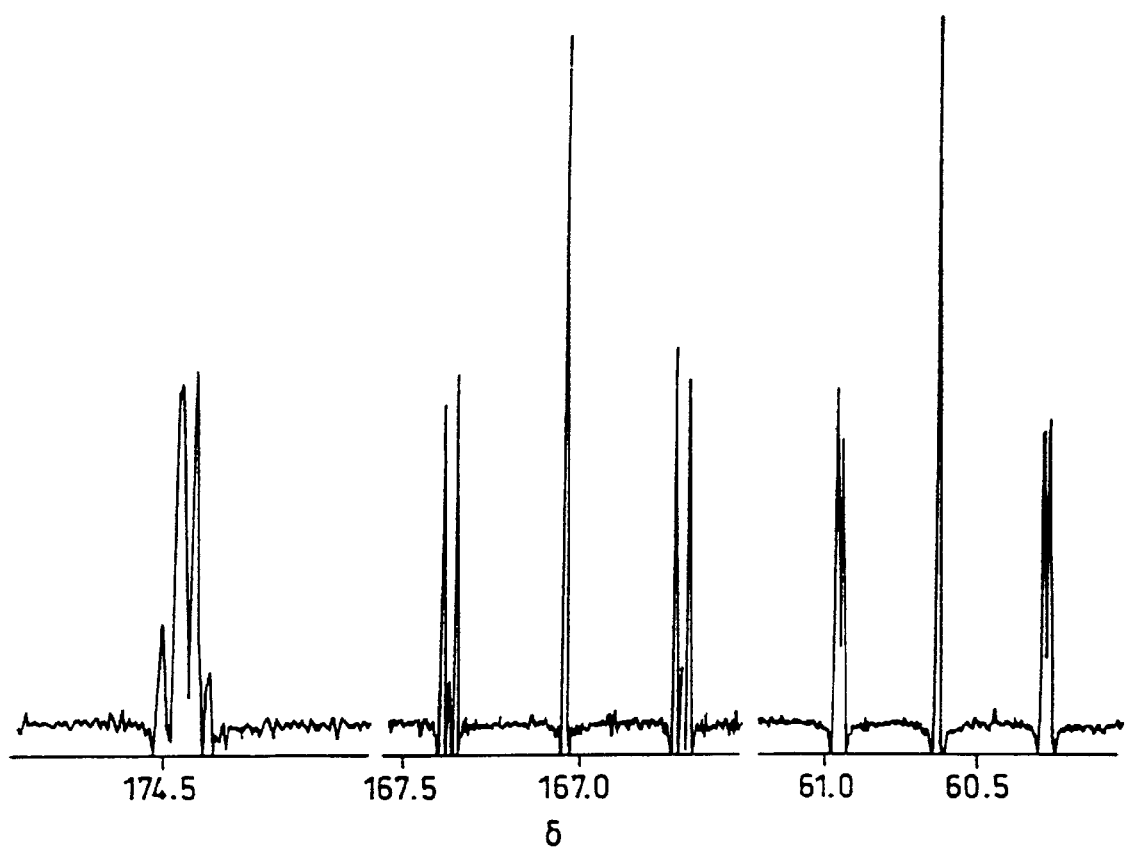
FIG. 3 shows $^{13}$C-NMR spectrum of carbons 7, 10 and 3 of benzyl clavulanate from feeding B. $J_{7,10}$3.8, $J_{3,7}$1.9, and $J_{3,10}$67.2 Hz.

In the three samples where $^{13}$C-enrichment was observed [compounds (A), (B) & (C)], it was noted that enrichment was specific to carbons 3, 7, and 10 of clavulanate with $^{13}$C—$^{13}$C spin-spin couplings being observed between all three labelled centres (FIG. 3 $^{13}$C-N.m.r. spectrum of carbons 7,10, and 3 of benzyl clavulanate from feeding B. J$_{7,10}$ 3.8, J$_{37}$ 1.9, and J$_{3,10}$ 67.2 Hz) indicating that bond breakage had not occurred during incorporation. These results lead us to the conclusion that (A), (B) and (C) are precursors in the biosynthesis of proclavaminic acid, and hence clavulanic acid, and that logically they occur in the pathway in that order.

In the case of G and 8 there was no enrichment under these experimental conditions. However by using methods for β-lactam ring formation well known in the art (for example ref 1) to convert G and 8 (or protected derivatives thereof) to C and proclavaminic acid respectively these compounds could be useful for the production of clavams, for example clavulanic acid, for example in a synthetic or semi-synthetic process.

The transformation of (C) to proclavaminic acid could be mediated by an arginase - type enzyme. Accordingly, evidence for this enzymatic activity was sought. It was found that cell-free preparations of S. clavuligerus ATCC 27064 were able to convert one of the enantiomers of racemic (C) quantitatively to proclavaminic acid (5) and urea. The activity was enhanced in the presence of $Mn^{2+}$, a phenomenon reported for arginases from Bacillus anthracis[7] and staphyloccal[7,8] sources. (2S)-(B), prepared from the corresponding (2S)-amino derivative,[1] was also hydrolysed under these conditions, but much less rapidly than (C), whereas no hydrolysis could be detected for (A) or (G). Clearly this enzyme is able to discriminate efficiently between the guanidino groups of these early biosynthetic precursors. Since the absolute stereochemistry of natural proclavaminic acid is (2S,3R), the enantiomer of (C) which is the substrate for amidino hydrolase will also presumably have the (2S,3R) stereochemistry.

Amidino hydrolase was purified according to section 1.2 above. The pure enzyme did not hydrolyse arginine to ornithine and is therefore different to the arginase previously reported in S. clavuligerus[9]. The N-terminal amino acid sequence of amidino hydrolase correlated with the open reading frame of the arnidino hydrolase related-gene in the clavulanic acid genetic cluster. The $M_r$ for the amidino hydrolase calculated from the DNA sequence was 33,374. From the above data it is concluded that (2S,3R)-(C) is probably converted directly to (2S,3R)-proclavarninic acid in the biosynthetic pathway to clavulanic acid.

The lower level of incorporation of $^{13}C$-labelled (A) compared with (B) and (C) indicates that either the compound is less efficiently transported into the cells, or that the true intermediate is possibly a derivative of (A), such as a coenzyme A thioester, which might favour ring closure. The result with (A) indicates that the generation of the β-lactam of (B) is by a biochemically unprecedented process, i.e. by amide bond formation, whereas the literature indicates that the precursors of the other monocyclic plactams, the nocardicins[10] and probably monobactams[10,11], already have the amide bond formed prior to ring closure. In these compounds ring closure is by $S_N2$ displacement of a seryl hydroxyl function.

Previous labelling studies have shown that the β-lactam carbons of clavulanic acid are derived from the glycolytic pathway, with pyruvate[12] being specifically incorporated into the β-lactam ring. We have also found that lactate is specifically incorporated into the β-lactam ring.

Hence, the $C_3$ moieties of (A), (B) and (C) would be derived from the same pathway. It is known that pyruvate and lactate can be biochemically converted to acrylate[13] and malonic semialdehyde.[14] Enzymatically catalysed Michael addition of arginine to acrylate, or Schiffs base addition with malonic semialdehyde, followed by reduction would yield precursor (A) in either case. The possible derivation of (A) from the reaction of arginine with malonic semialdehyde is of particular interest as it bears a strong resemblance to the biosynthesis of the opine metabolites, where similar Schiffs base formation and subsequent reduction occur.[15]

The evidence presented indicates that, the β-lactam ring of proclavaminic acid is constructed in a novel manner involving an amide forming reaction; that the arginine derivatives (2S)-(B) and (2S,3R)-(C) are the biosynthetic precursors of proclavaminic acid, that (2S)-(B) is hydroxylated to (2S,3R)(C) and that the enzyme amidino hydrolase is a new enzyme (now named proclavaminic acid amidino hydrolase)hydrolyses (2S,3R) -(C) to proclavaminic acid.

Conclusion

Experiments 1 and 3 show that arginine, B and C are on the pathway to proclavaminic acid and hence to clavulanic acid and shows that arginine is a more immediate precursor of clavulanic acid relative to ornithine.

References.

1. K. H. Baggaley, S. W. Elson, N. H. Nicholson,and J. T. Sime, J. Chem. Soc. Perkin I 1990 1521 and references cited therein.
2. A. E. Miller and J. J. Bischoff, Synthesis, 1986, 777, K. Kim, Y-T Lin and H. S. Mosher, Tetrahedron Lett., 1988, 29, 3183.
3. R. L. Heinrikson and S. C. Meredith, Anal. Biochem., 1984, 136,65, and Waters Associates commercial literature.
4. S. Sakaguchi, Nature, 1953,172,1 100.
5. S. W. Elson, K. H. Baggaley, J. Gillett, S. Holland, N. H. Nicholson, J. T. Sime, and S. R. Woroneicki, J. Chem. Soc., Chem. Commun., 1987, 1739,
6. G. Stork, A. Y. W. Leong and A. M. Touzin. J. Org. Chem., 1976, 41, 3491.
7. E. Soru, J. Chromatog., 1965, 20, 325.
8. E. Sora and O. Zaharia, Rev. Roum. Biochem., 1976, 13, 29.
9. J. Romero, P. Liras, and J. F. Martin, Applied and Environrnental Microbiology, 1986,52, 892
10. C. A. Townsend, A. M. Brown, and L. T. Nguyen, J. Amer. Chem. Soc., 1983, 105,919.
11. J. O'Sullivan, A. M. Gillum, C. A. Aklonis, M. L. Souser, and R. B. Sykes, Antimicrobial Agents and Chemotherapy, 1982, 21,558.
12. S. W. Elson and R. S. Oliver, J. Antibiot., 1978,31, 586. S. W. Elson in 'Recent Advances in The Chemistry of βLactam Antibiotics' Ed. G. I. Gregory, Royal Society of Chemistry; London, 1981, pages 142–150.
13. R. D. Kuchta and R. H. Abeles, J. Biol. Chem., 1985, 260, 13181.
14. P. R Vaglos and J. M. Earl, J. Biol. Chem., 1959, 234,2272.
15. J. Thompson and S. P. F. Miller, Adv. Enzymol. Relat. Areas Mol. Biol., 1991, 64,317.
16. K. L. Kaestle, M. K. Anwer, T. K Audhya and G. Goldstein, Tetrahedron Leters, 1991, 32,327.

We claim:

1. A process for preparing clavulanic acid which comprises selecting, a compound from compounds of formula (I)

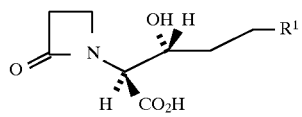 (I)

wherein R¹ is

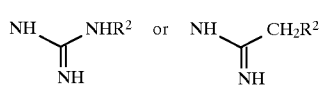

wherein $R^2$=H or $C_{1-6}$ alkyl or compounds of formula (II)

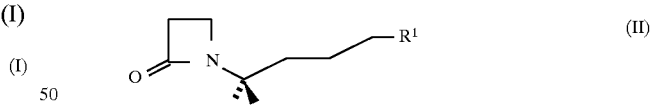 (II)

wherein R¹ is

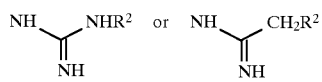

where $R^2$=H or $C_{1-6}$ alkyl or compounds of formula (E)

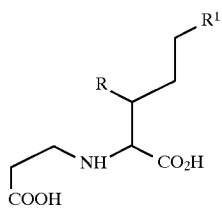

wherein R is H or OH
and wherein $R^1$ is

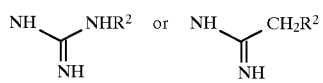

where $R^2$=H or $C_{1-6}$ alkyl,
and treating said compound with an enzyme system from Streptomyces.

2. A process as claimed in claim 1 wherein the enzyme system comprises one or more of clavaminic acid synthase and amidino hydrolase.

3. A process for the production of clavulanic acid which comprises preparing proclavaminic acid by the action of one or more enzymes from an enzyme system from Streptomyces on threo-3-hydroxy-5-guanidino-2-(2-oxo-azetidin-1-yl) pentanoic acid and converting said proclavaminic acid to clavulanic acid.

4. A process as claimed in claim 3 which further comprises preparing threo-3-hydroxU-5-guanidino-2-(2-oxo-azetidin-1-yl) pentanoic acid by the action of one or more enzymes from an enzyme system from Streptomyces on (2S)-5-guanidino-2-(2-oxo-azetidin-1-yl) pentanoic acid or $N^2$-(2-carboxyethyl)-3-hydroxy-arginine.

5. A process as claimed in claim 4 which further comprises preparing (2S)-5-guanidino-2-(2-oxo-azetidin-1-yl) pentanoic acid by the action of one or more enzymes on $N^2$-(2-carboxyethyl)-(S)-arginine.

6. A compound of formula (I) or a salt or protected form thereof:

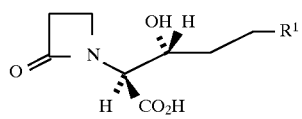

wherein $R^1$ is

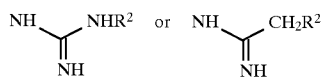

wherein $R^2$=H or $C_{1-6}$ alkyl.

7. A compound as claimed in claim 6 which is threo-3-hydroxy-5-guanidino-2-(2-oxo-azetidin- 1-yl) pentanoic acid.

8. A process for preparing threo-3-hydroxy-5-fzuanidino-2-(2-oxo-azetidin-1-yl) pentanoic acid which comprises reacting

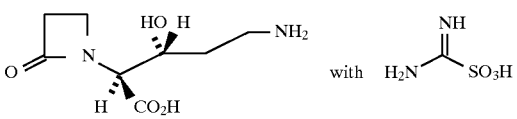

9. A compound of formula (II) or a salt or protected form thereof:

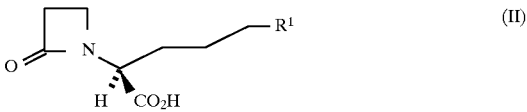

wherein $R^1$ is

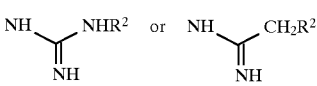

where $R^2$=H or $C_{1-6}$ alkyl.

10. A compound as claimed in claim 9 which is (2S)-5-guanidino-2-(2-oxo-azetidin-1-yl) pentanoic acid.

11. A process for beta-hydroxylation of compounds of the formula (II) as defined in claim 9, alpha-amino acids or N-acyl derivatives thereof, in which the alpha-amino acid substrate carries an amino, guanidino or amidino group in the side chain which comprises incubating the substrate with clavaminic acid synthase.

12. A process as claimed in claim 11 wherein the N-acyl amino acid is N-acetyl arginine or N- acetyl ornithine.

13. A compound of formula III or a salt or protected form thereof:

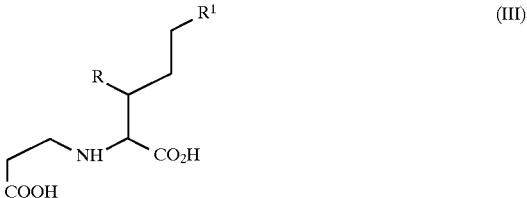

wherein R is H or OH
and wherein $R^1$ is

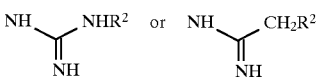

where $R^2$=H or $C_{1-6}$ alkyl.

14. A compound as claimed in claim 13 which is $N^2$-(2-carboxyethyl)-(S)-arginine or $N^2$-(2-carboxyethyl)-3-hydroxy-arginine.

15. A process for preparing (2S)-5-guanidino-2-(2-oxo-azetidin-1-yl) pentanoic acid which comprises contacting $N^2$-(2-carboxyethyl)-(S)-arginine, or an activated derivative thereof, with an enzyme system from Streptomyces.

16. A process according to claim 15, in which an ester or CoA thioester of $N^2$-(2-carboxyethyl)-(S)-arginine is used.

17. A process for preparing (2S)-5-guanidino-2-(2-oxo-azetidin-1-yl) pentanoic acid by reacting

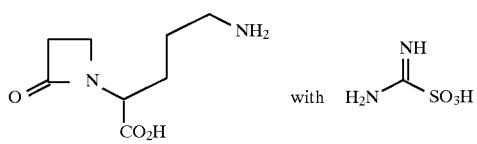

with

18. A process for preparing E-(2S)-5-amino-2-(2'-oxoazetidin-1'-yl) pent-3-enoic acid which comprises incubating 5-amino-2S-(2-oxo-azetidin-1-yl) pentanoic acid with clavaminic acid synthase.

19. An enzyme having amidino hydrolase activity obtained by treating *Streptomyces clavuligerus* mycelium, by centrifugation and ultrasonification followed by fractionation by ion-exchange chromatography.

20. An enzyme according to claim 19 which comprises the sequence of amino acids shown in SEQ ID NO: 1.

21. A process for preparing threo-3-hydroxy-5-guanidino-2-(2-oxo-azetidin-1-yl) pentanoic acid which comprises contacting (2S)-5-guanidino-2-(2-oxo-azetidin-1-yl) pentanoic acid or a salt or protected form thereof with an enzyme having hydroxylation activity.

22. A process as claimed in claim 21, in which said enzyme is clavaminic synthase.

23. The compound E-(2S)-5-amino-2-(2'-oxoazetidin-1'-yl)pent-3-enoic acid.

24. An isolated DNA selected from the group consisting of:

(a) a gene encoding an enzyme having amidino hydrolase activity obtained by treating *Streptomyces clavuligerus* mycelium by centrifugation and ultrasonification followed by fractionation by ion-exchange chromatography;

(b) a gene encoding the amino acid sequence shown in SEQ ID NO: 1;

(c) a gene having the nucleic acid sequence shown in SEQ ID NO: 2;

(d) a DNA which hybridizes under conditions of high stringency with any of the DNAs of (a), (b) or (c) but excluding a DNA of length of about 60 kb or greater.

25. A process for preparing compounds containing a 7-oxo-4-oxa-1-azabicyclo heptane nucleus which comprises selecting a compound from compounds of formula (I)

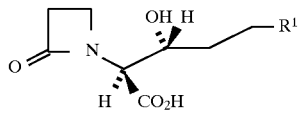

wherein $R^1$ is

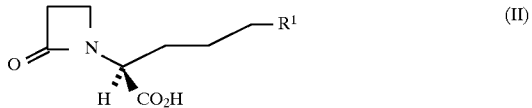

wherein $R^2$=H or $C_{1-6}$ alkyl or compounds of formula (II)

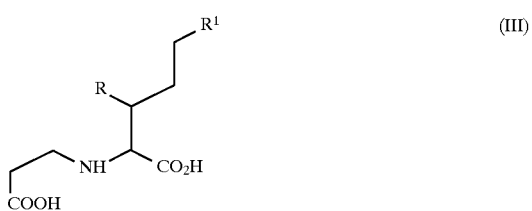

wherein $R^1$ is

NH   NHR²     or    NH   CH₂R²
 ‖                    ‖
 NH                   NH where $R^2$=H or $C_{1-6}$ alkyl or compounds of formula (III)

(III)

wherein R is H or OH
and wherein $R^1$ is

NH   NHR²     or    NH   CH₂R²
 ‖                    ‖
 NH                   NH where $R^2$=H or $C_{1-6}$ alkyl, and treating said compound with an enzyme system from Streptomyces.

26. A process as claimed in claim 25 wherein the enzyme system comprises one or more of clavaminic synthase and amidino hydrolase.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 313 amino acids
        ( B ) TYPE: amino acid
        ( D ) TOPOLOGY: unknown ( i i ) MOLECULE TYPE: protein ( i i i ) HYPOTHETICAL: YES ( v ) FRAGMENT TYPE: N-terminal ( v i ) ORIGINAL SOURCE:
        ( A ) ORGANISM: Streptomyces clavuligerus
        ( B ) STRAIN: Re-isolate of S. clavuligerus ATCC 27064

( x i ) SEQUENCE DESCRIPTION: SEQ ID NO: 1:

```
Met Glu Arg Ile Asp Ser His Val Ser Pro Arg Tyr Ala Gln Ile Pro
 1               5                  10                  15
Thr Phe Met Arg Leu Pro His Asp Pro Gln Pro Arg Gly Tyr Asp Val
            20                  25                  30
Val Val Ile Gly Ala Pro Tyr Asp Gly Thr Ser Tyr Arg Pro Gly
            35              40                  45
Ala Arg Phe Gly Pro Gln Ala Ile Arg Ser Glu Ser Gly Leu Ile His
    50                  55                  60
Gly Val Gly Ile Asp Arg Gly Pro Gly Thr Phe Asp Leu Ile Asn Cys
65                      70                  75                  80
Val Asp Ala Gly Asp Ile Asn Leu Thr Pro Phe Asp Met Asn Ile Ala
                85                  90                  95
Ile Asp Thr Ala Gln Ser His Leu Ser Gly Leu Leu Lys Ala Asn Ala
                100                 105                 110
Ala Phe Leu Met Ile Gly Gly Asp His Ser Leu Thr Val Ala Ala Leu
            115                 120                 125
Arg Ala Val Ala Glu Gln His Gly Pro Leu Ala Val Val His Leu Asp
    130                 135                 140
Ala His Ser Asp Thr Asn Pro Ala Phe Tyr Gly Gly Arg Tyr His His
145                 150                 155                 160
Gly Thr Pro Phe Arg His Gly Ile Asp Glu Lys Leu Ile Asp Pro Ala
                165                 170                 175
Ala Met Val Gln Ile Gly Ile Arg Gly His Asn Pro Lys Pro Asp Ser
                180                 185                 190
Leu Asp Tyr Ala Arg Gly His Gly Val Arg Val Val Thr Ala Asp Glu
                195                 200                 205
Phe Gly Glu Leu Gly Val Gly Gly Thr Ala Asp Leu Ile Arg Glu Lys
            210                 215                 220
Val Gly Gln Arg Pro Val Tyr Val Ser Val Asp Ile Asp Val Val Asp
225                 230                 235                 240
Pro Ala Phe Ala Pro Gly Thr Gly Thr Pro Ala Pro Gly Gly Leu Leu
                245                 250                 255
Ser Arg Glu Val Leu Ala Leu Leu Arg Cys Val Gly Asp Leu Lys Pro
                260                 265                 270
Val Gly Phe Asp Val Met Glu Val Ser Pro Leu Tyr Asp His Gly Gly
            275                 280                 285
Ile Thr Ser Ile Leu Ala Thr Glu Ile Gly Ala Glu Leu Leu Tyr Gln
            290                 295                 300
Tyr Ala Arg Ala His Arg Thr Gln Leu
305                 310
```

( 2 ) INFORMATION FOR SEQ ID NO: 2:

( i ) SEQUENCE CHARACTERISTICS:
( A ) LENGTH: 942 base pairs
( B ) TYPE: nucleic acid
( C ) STRANDEDNESS: double
( D ) TOPOLOGY: unknown ( i i ) MOLECULE TYPE: DNA (genomic)

( i i i ) HYPOTHETICAL: NO ( v i ) ORIGINAL SOURCE:
( A ) ORGANISM: Streptomyces clavuligerus
( B ) STRAIN: Reisolate of S. clavuligerus ATCC 27064

( x i ) SEQUENCE DESCRIPTION: SEQ ID NO: 2:

| | | | | | | |
|---|---|---|---|---|---|---|
| GTGGAGCGCA | TCGACTCGCA | CGTTTCACCC | CGCTACGCAC | AGATCCCAC | CTTCATGCGC | 60 |
| CTGCCGCACG | ATCCCCAGCC | CCGCGGCTAT | GACGTGGTGG | TCATCGGAGC | CCCCTACGAC | 120 |
| GGGGGCACCA | GCTACCGTCC | CGGCGCCCGG | TTCGGCCCCC | AGGCCATCCG | CAGTGAGTCG | 180 |
| GGCCTCATCC | ACGGTGTCGG | CATCGACCGG | GGCCCCGGCA | CGTTCGACCT | GATCAACTGT | 240 |
| GTCGACGCCG | GGGACATCAA | TCTGACGCCG | TTCGACATGA | ACATCGCGAT | CGACACGGCG | 300 |
| CAGAGCCATC | TGTCGGGCCT | GCTGAAGGCC | AACGCCGCCT | TTCTGATGAT | CGGCGGCGAC | 360 |
| CACTCGCTGA | CGGTGGCCGC | CCTGCGCGCG | GTCGCGGAGC | AGCACGGCCC | GCTCGCCGTG | 420 |
| GTGCACCTGG | ACGCGCACTC | CGACACCAAC | CCGGCCTTCT | ACGGGGCCG | GTACCACCAC | 480 |
| GGCACCCCCT | TCCGGCACGG | GATCGACGAG | AAGCTGATCG | ACCCGGCGGC | GATGGTCCAG | 540 |
| ATCGGCATCC | GGGGCCACAA | CCCGAAGCCG | GACTCGCTCG | ACTACGCCCG | GGGCCACGGC | 600 |
| GTCCGGGTGG | TCACGGCGGA | CGAGTTCGGC | GAGCTGGGGG | TGGGCGGGAC | CGCCGACCTC | 660 |
| ATCCGCGAGA | AGGTCGGCCA | GCGGCCCGTG | TACGTCTCGG | TCGACATCGA | CGTGGTCGAC | 720 |
| CCCGCCTTCG | CCCCCGGTAC | GGGCACGCCC | GCGCCGGGCG | GGCTCCTCTC | GCGCGAGGTG | 780 |
| CTGGCGCTGC | TGCGCTGCGT | GGGTGACCTG | AAGCCGGTCG | GCTTCGACGT | GATGGAGGTG | 840 |
| TCACCCCTCT | ACGACCACGG | CGGGATCACT | TCGATCCTGG | CCACGGAGAT | CGGTGCGGAA | 900 |
| CTGCTCTACC | AGTACGCCCG | AGCCCACAGA | ACCCAGTTGT | GA | | 942 |